United States Patent [19]

Karlsson et al.

[11] Patent Number: 4,980,462
[45] Date of Patent: Dec. 25, 1990

[54] ANTIVIRAL AGENTS

[75] Inventors: Karl-Anders Karlsson, Gothenburg; Erling Norrby, Lidingo; Göran Wadell, Umeå, all of Sweden

[73] Assignee: Symbicom Aktiebolag, Umea, Sweden

[21] Appl. No.: 368,188

[22] Filed: Jun. 19, 1989

Related U.S. Application Data

[63] Continuation of Ser. No. 916,542, filed as PCT DM86/00007 on Jan. 13, 1986, published as WO86/03971 on Jul. 16, 1986, Pat. No. 4,859,769.

[30] Foreign Application Priority Data

Jan. 14, 1985 [DK] Denmark .............................. 178/85

[51] Int. Cl.$^5$ ...................... A61K 37/22; C07H 15/00; G01N 33/53
[52] U.S. Cl. ...................... 536/53; 424/520; 514/25; 514/53; 514/613; 514/625; 536/1.1; 536/4.1; 536/54; 536/55; 536/115; 536/116; 536/118; 536/120; 536/122
[58] Field of Search .............. 536/1, 1.1, 4, 4.1, 536/53, 54, 55, 115, 116, 118, 120, 122; 424/95; 514/24, 53, 613, 625

[56] References Cited

U.S. PATENT DOCUMENTS

| | | | |
|---|---|---|---|
| 3,622,666 | 11/1971 | Cook | 514/25 |
| 4,397,959 | 8/1983 | Hechemy | 435/38 |
| 4,446,128 | 5/1984 | Baschang et al. | 536/53 |
| 4,678,747 | 7/1987 | Lloyd et al. | 435/7 |
| 4,695,553 | 9/1987 | Wardlaw et al. | 435/7 |
| 4,711,841 | 12/1987 | Kronvall | 437/7 |
| 4,724,205 | 2/1988 | Karlsson et al. | 536/53 |

Primary Examiner—Ronald W. Griffin
Attorney, Agent, or Firm—Iver P. Cooper

[57] ABSTRACT

A second-step virus binding receptor is found in nature on the surface of animal and plant cells. This receptor is thought to be needed for virus penetration into target cells. The second-step receptor has been found to bind a wide variety of viruses belonging to a number of different families. The second-step receptor and natural or synthetic substances which correspond to or are analogous to the binding epitope of the second-step receptor in that they are able to bind to a site on the virus which recognizes the binding epitope of the natural second-step receptor, are therefore indicated for the diagnosis, prophylaxis or treatment of viral infections.

15 Claims, 9 Drawing Sheets

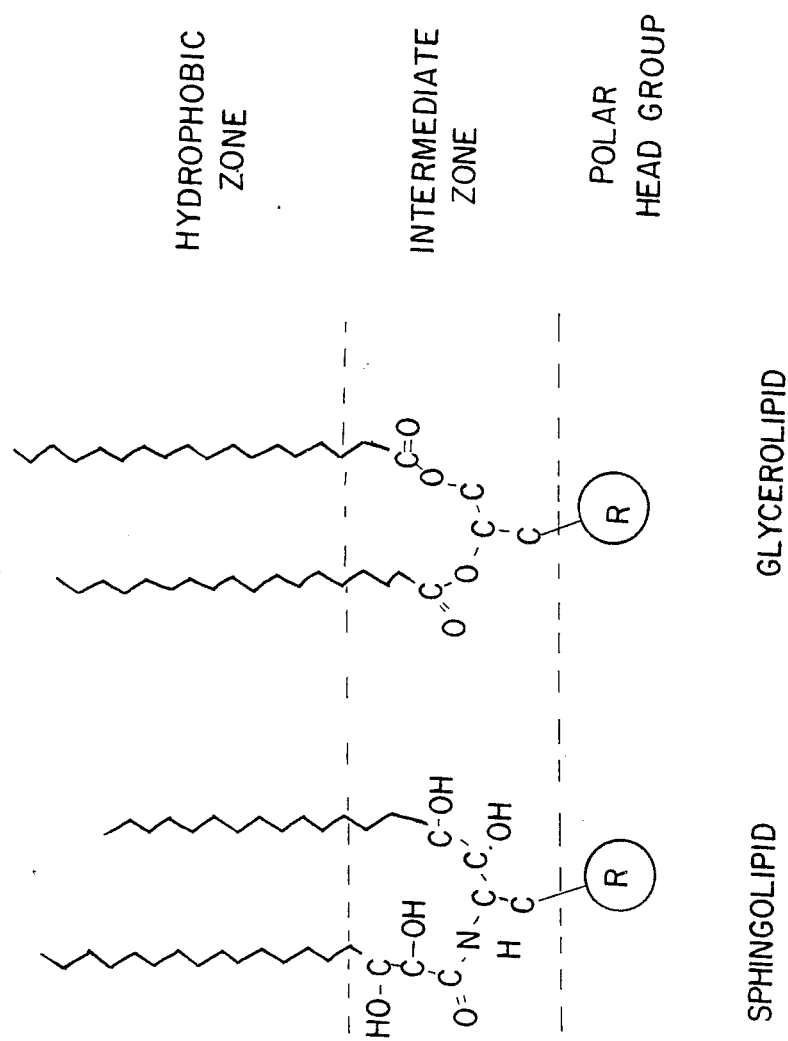

ly been employed, it has not always been possible to develop a
ANTIVIRAL AGENTS This application is a continuation of Ser. No. 06/916,542, filed Nov. 5, 1986, now patented, U.S. Pat. No. 4,859,769. Ser. No. 916,542 is the national stage of PCT/DK86/00007, which has an international filing date of Jan. 13, 1986. This date is the effective filing date of Ser. No. 916,542 pursuant to 35 U.S.C. 120,363.

The present invention relates to the use of certain compounds with virus-binding properties for the diagnosis, prophylaxis or treatment of viral infections, as well as antiviral agents and pharmaceutical compositions comprising these compounds.

Despite the extensive damage to animals, including human beings, and plants caused by viruses, no general rational therapy has yet been devised against viral infections comparable to, e.g., antibiotic treatment in the case of bacterial infections. Although, in certain cases, a prophylactic approach in the form of a vaccine causing immunization and, in most instances, producing resistance to re-infection for life has successfully been employed, it has not always been possible to develop a vaccine of a sufficiently broad applicability to be effective against a wide variety of strains of the same viral species; this, for instance, has been a problem with the influenza vaccines which have hitherto been devised, so that immunization has occurred against the specific strain on which the vaccine has been based, but not against other, closely related strains with slightly different antigenic properties.

In recent years, increasing attention has been paid to the importance, for a variety of biological interactions, of so-called receptors. Receptors, which are often glycolipids or glycoproteins, that is, consist of a carbohydrate portion linked to a lipid or a protein, form integral parts of the plasma membrane of animal and plant cells, being located on the surface of the cell membrane of a wide variety of cells. Their function as specific receptors for a wide range of biological entities is extremely diverse. Due to their carbohydrate portion being exposed on the surface of the cell membrane, they may have antigenic properties or function as cell surface markers; they may confer structural rigidity to the outer monolayer of the membrane lipid bilayer; they may form part of a system for cell-cell interaction and recognition; or they may play a part in the interaction of the cell with bioactive factors such as bacterial toxins, glycoprotein hormones or microorganisms, anchoring these to the cell surface. For instance, it is known that there is a connection between such receptors and bacterial infections in that receptor analogues may be used to inhibit the bacterial adhesion necessary to effect an infection.

For a viral infection to become established, the viral genome has to penetrate into the host cell. For some membrane-enveloped (having a membrane around the nucleocapside) viruses, this process is known to involve a two-step mechanism, namely the sequential attachment to and penetration into the host cell (see reference 1; the list of references is given below in the section entitled "Bibliography"). It is known that the attachment is due to a receptor located on the surface of target cells for viral infection (see reference 3). It has commonly been assumed that the penetration step is a logical consequence of the attachment, producing spontaneous fusion at the surface membrane or penetration after receptor-mediated endocytosis. In some cases, a second interaction has been considered, but this is of a less specific kind than the attachment, mainly a hydrophobic interaction with the membrane interior (see reference 2). In the course of the research leading to the present invention, however, it has surprisingly been found that, on the contrary, where certain viruses are concerned, the second binding is specific, being ascribable to a specific substance with definable chemical characteristics. This binding substance is therefore comparable to the known first-step receptors (see reference 3) which mediate attachment of the virus to the host cell, and is analogously termed the second-step receptor. It seems likely that both the first-step and the second-step receptors are required on a cell for infection to occur. The principal difference between the two receptors is that the first-step receptor is present on the specific cell type which is prone to infection with a particular species of virus, while the second-step receptor is present on all cells which are the ports-of-entry of viral infections in general (i.e. this receptor is not specific to a particular viral species). Thus, a virus selects its host cell or tissue by means of the first-step receptor, but uses a generally available receptor for penetration.

It is further assumed that the second-step receptor is required for viral survival. Without membrane penetration into the cytoplasm, the attached viral particle would ultimately be degraded in the lysosomes through the efficient cleaning machinery of the cell. The second-step receptor-binding property is therefore assumed to be a highly conserved (genetically stable so that it does not change, conversely to the antigenic properties of the virus) property of the virus, regardless of the nature of the first-step receptor.

A supporting argument in favour of the presence of the second-step receptor is the fact that a hydrophobic part of the virus, for instance a hydrophobic peptide sequence such as the peptide sequence constituting the binding site on the virus, cannot spontaneously penetrate into the host cell membrane because of the natural resistance of the membrane. The natural surface membrane is constructed to avoid non-regulated uptake of hydrophobic and other substances. This would otherwise seriously interfere negatively with the membrane functions. Many regulatory substances in the organism such as hormones are hydrophobic, and their uptake is mediated by specific receptors and not by mere solubility in the lipid bilayer of the cell membrane. Therefore, analogously, a virus particle in need of hydrophobic penetration must utilize a bilayer-close receptor which means that an attachment to the first-step receptor is not sufficient in itself.

The seemingly paradoxical phenomenon that a virus receptor common to many cells allows an infection of certain cells only may be explained by the complex nature of the host cell surface which has a layer of glycoconjugates extending 100 Å or more from the lipid bilayer. The second-step receptor is located immediately adjacent to the bilayer and is therefore assumed to be hidden from direct contact from the outside. The first-step receptors, on the other hand, are located at a greater distance from the bilayer and are therefore immediately accessible for binding. It is presumed that this first-step binding allows a proximation of the virus particle to the bilayer-close second-step receptor which is exposed by the well-known phenomenon of lateral mobility of surface components which is partly induced by repulsion from the virus surface due, for instance, to negative electrical charging (see reference 4). The binding of the virus to the second-step receptor therefore requires a first-step attachment which defines the cell specificity of infection.

The purpose of the present invention is to utilize this basic research concerning first-step and second-step binding to employ the natural second-step receptors as such to compete with the second-step receptors present on potential host or target cells for the binding sites on the virus, and by blocking these sites prevent viral penetration into the cells so that viral infection may be prevented or controlled, as well as develop compounds which, because they mimic the binding characteristics of the natural receptor, fulfil the same function of binding to and blocking the binding sites on the virus. It is preferred for the present purpose to employ the second-step receptors or similar compounds rather than the first-step receptors, as the former are less specific and therefore have a broader (more general) applicability.

Accordingly, the present invention relates to the use of a compound comprising at least one portion, which, with respect to its conformation and properties, corresponds to or is analogous to the binding epitope of a second-step virus-binding receptor on an animal or plant cell in that this portion is capable of binding to a site on a virus which recognizes the binding epitope of the second-step binding receptor, for the manufacture of a composition for the diagnosis, prophylaxis or treatment of viral infections.

In the present context, the term "binding epitope" is intended to mean the smallest possible part of the receptor to interact with the virus. In nature, this binding epitope is carried on the second-step receptor of cells which are targets of viral infections, which receptors are generally glycolipids. The existence of the second-step receptor comprising such a binding epitope has been demonstrated by the present inventors by means of an assay in which potential receptors in glycolipid form extracted from target cells for infection are separated on a surface (chromatogram) which by a suitable treatment is made to resemble the biological cell membrane. This means that the potential receptor substances are likely to be exposed in the assay in a similar way to the presentation on the living cell. The results from this assay therefore compare well with binding results from intact cells or tissues. The assay has revealed the presence of first-step and second-step receptors, and has furthermore revealed those receptor candidates which actually do effect binding.

The findings from this assay contradict previously published results which are based on assays in which extracted substances in solubilized micellar form are used to inhibit virus attachment to host cells to provide information on activity. These assays often produce unspecific binding and therefore do not adequately reflect the actual binding mechanisms present on the cell surface.

For instance, reference 6 describes the inhibition of hemolysis (leakage of red blood cells) induced by Sendai virus by means of several long-chain fatty acids, that is, an apparent effect on virus penetration. Free fatty acids, however, are not components of the surface membrane. It seems that, in this case, the hydrophobic paraffin chains interact unspecifically with the hydrophobic peptide sequence of the F glycoprotein (defined below). Two papers (see reference 7) report the inhibition of rhabdovirus by phosphatidylserine and other phospholipids. Finally, two papers by Huang (see reference 8) show inhibition of hemolysis caused by Sendai virus and Fowl plague virus using phospholipids and some natural and synthetic glycolipids. Thus, it was possible to inhibit Sendai virus-induced hemolysis using fatty acids, or phospholipids, or glycolipids, presented in micellar form. As noted, no binding of Sendai virus by free fatty acids, phospholipids or the natural or synthetic glycolipids used by Huang was found when using the assay developed by the present inventors as described above. The three groups of substances are active at comparable levels, but the polar head groups of the two latter are structurally too different to explain a specific interaction of the virus with this part. Therefore, the most likely explanation is that the common part of these substances, the lipid chains, interacts hydrophobically in an unspecific way with the hydrophobic parts of the virus, most likely the N-terminal peptide of the F glycoprotein. This means that the substances used by previous researchers cannot be genuine receptors on the host cells. In case of the phospholipids, this conclusion is supported by the number of receptor sites, $10^6$, found on target cells, which is several orders of magnitude too low to correspond to phospholipid, a very common cell surface component.

In brief, the data presented in the literature published to date may be explained by an unspecific hydrophobic interaction of the tested substances with a limited number of viruses. Although this interaction may theoretically occur with a part of the same peptide inferred below to bind specifically to the second-step receptor with a structurally defined binding epitope, there is no evidence presented in these references for genuine receptor specificity. Furthermore, the hydrophobic interaction recognized is common in many systems. One example is fatty acids of different structures associated with albumin, the major protein in blood plasma of mammals. Therefore, the referred findings cannot be employed for the purposes of the present invention due to the generality of simple hydrophobic interactions.

By means of the assay developed by the present inventors, it has therefore become possible, for the first time, to define specific substances which are useful as second-step receptors. Thus, as mentioned above, in the assay there is an absence of binding to other membrane components which have been claimed by other researchers (cf. the references indicated above) to bind the viruses analyzed. For instance, there is no binding to free fatty acids/lipids or free carbohydrates, both of which are components of the natural second-step receptor, nor to phospholipids like phosphatidylcholine, sphingomyelin, phosphatidylethanolamine or phosphatidylserine, using relevant levels of receptor material. Therefore, the specificity of the assay employed by the present inventors has made it possible to define the structure of the second-step receptor by avoiding the misleading results obtained by other assay techniques, principally the unspecific interaction between the components employed in the traditional assays.

On the basis of the substances found to be receptor-active in the assay described above, certain general characteristics of the binding epitope have been established. Thus, the compounds used for the purposes of the present invention should comprise a hydrophobic part, a polar part adjacent to the hydrophobic part and a part which is both polar and hydrophobic adjacent to the polar part. Furthermore, it has been established that these three parts should form a continuous surface with a total length of about 15–20 Å and a width of about 8–10 Å.

In accordance with the present invention, the hydrophobic part may comprise a hydrocarbon moiety presenting a hydrophobic surface with a surface area of at least about 50–80 Å². This surface area has been found sufficient to establish a hydrophobic interaction between the binding site on the virus and the hydrophobic part of the binding epitope, but of course the hydrocarbon moiety may extend over a larger area which may be practical for some applications where the receptor is to be coupled to a carrier (see below). It is, however, important to note that a larger surface area of the hydrocarbon moiety does not contribute to the binding epitope itself. The polar/hydrophobic part should preferably include a structure corresponding to the α side of the hexose occurring in the natural binding epitope. This α side constitutes the "hydrophobic" side of the saccharide. The polar part which forms an intermediate zone between the hydrophobic part and the polar/hydrophobic part should comprise at least two hydrogen-bonding sites. The intermediate zone may carry both hydrogen bond donors and hydrogen bond acceptors.

The polar/hydrophobic part may comprise a homo- or heterocyclic structure and is preferably a monosaccharide which is optionally suitably substituted in such a way that the substituent does not interfere sterically with the structure corresponding to the α side of the hexose occurring in the natural binding epitope. Experiments have established that substitutions that block the binding protrude from the same side as the α side of this hexose, while substitutions allowing a binding protrude in other directions which indicates a steric specificity in the approach from the virus. The substituent may, for instance, be a saccharide. Preferably, the monosaccharide has the conformation of β-galactopyranose or β-glucopyranose, at least in the receptor-active part thereof, and is preferably a hexose although a pentose or heptose may also be employed for this purpose. The hexose may be galactose or glucose which are the hexoses occurring in the most optimal natural second-step receptor.

The hydrophobic part comprised by the hydrocarbon moiety need have no structural specificity as it does not appear to be essential for primary epitope recognition and hydrogen bond breaking of membrane resistance which is effected by the polar/hydrophobic part and the polar part, respectively. However, the hydrophobic part is important for an extended hydrophobic interaction between the binding site on the virus and the cell membrane and is therefore still needed in substances used to mimic the natural receptor as proper binding and therefore blocking of the site on the virus would otherwise not be effective. The hydrocarbon moiety may comprise a saturated or unsaturated, branched or linear, open-chain or cyclic hydrocarbon or a combination thereof. Preferably, however, the hydrocarbon moiety comprises one or two saturated or unsaturated, linear or branched hydrocarbons. Most preferably, the hydrocarbon is part of a ceramide as ceramide structures show a self-condensation effect in a monolayer of the surface balance (see reference 33), probably due to intermolecular hydrogen bonding. This may make the presentation of the binding epitope at a condensed surface important for efficient binding of a ligand, i.e. the virus. The ceramide should preferably comprise a 2-hydroxy fatty acid as this appears to improve the accessibility of the virus to the binding epitope in that, in certain of the receptor substances, it provides a suitable conformation and presentation of the binding epitope in a highly self-condensing monolayer with tight molecular packing due to intermolecular hydrogen bonding. The hydrocarbon moiety should have at least about 14 carbon atoms, but from a practical point of view (when providing sufficient hydrophobicity to bind the hydrocarbon moiety to a carrier by hydrophobic interaction (see below)), preferably about 20–30 carbon atoms.

As indicated above, the structure or conformation of the compound to be employed as the receptor substance or receptor substitute has been found to be critical for its efficiency in this respect. It has been found that the compound should have a bent or curved conformation with a polar/hydrophobic head group bending towards the plane of the monolayer formed by the hydrophobic part such as the hydrocarbon moiety. Accordingly, the compound preferably has a general conformation corresponding to that of the natural binding epitope carried by 1-O-β-D-galactopyranosyl-N-(2-D-hydroxyalkanoyl)-1,3-D-dihydroxy-2-D-aminoalkane which has the conformation of the approximate steric atomic relations described according to crystallographic conventions with a crystal unit cell of a=11.2 Å, b=9.3 Å, c=46.5 Å, and β=99°, and with the selected fractional atomic coordinates for x, y and z, respectively, for the hexose C1" 0.82, 0.99 and 0.42, C3" 0.91, 1.25 and 0.44, C5" 0.72, 1.15 and 0.46, for the long-chain base O1 0.80, 0.90 and 0.41, C1 0.76, 0.76 and 0.42, C2 0.78, 0.66 and 0.39, C5 0.61, 0.62 and 0.31, N1 0.90, 0.69 and 0.38, O2 0.57, 0.69 and 0.37, for the fatty acid C1' 0.98, 0.58 and 0.37, C2' 1.08, 0.64 and 0.36, C5' 1.17, 0.71 and 0.29O1' 0.95, 0.45 and 0.38, O2' 1.12, 0.79 and 0.37, the compound showing these atomic relations and coordinates or variants thereof which do not interfere with the binding activity, in that the compound comprises a polar/hydrophobic part (similar in structure to the part A shown in the conformation formula of the natural binding epitope) including a structure/conformation corresponding to the α side of the hexose ocurring in the natural binding eptiope and preferably comprising the D or L forms of a monosaccharide having the conformation of β-galactopyranose, at least in the receptor-active part, which monosaccharide is optionally suitably substituted at a position in which the substituent does not sterically interfere with the structure corresponding to the α side of the hexose occurring in the natural binding epitope, a polar part (similar in structure to part B shown in the conformation formula of the natural binding epitope) comprising at least two hydrogen-bonding sites which may be an amino, carbonyl, hydroxyl, sulfhydryl, sulfoxy or sulfone group, and a hydrophobic part (similar in structure to part C shown in the conformation formula of the natural binding epitope) comprising a saturated or unsaturated, branched or linear, open-chain or cyclic hydrocarbon or a combination thereof with a surface area of at least about 50–80 Å$^2$.

From what is outlined above, it appears that the structure of the binding epitope of the compound employed for the present purposes should preferably be one which closely mimics the conformation of the most optimal natural receptor as determined by X-ray crystallography (see reference 31). This natural receptor has a spoon-like or shovel-like conformation (apparent from the conformation formula shown above) with a hexose (A) bending towards the plane of the monolayer formed by the paraffin chains (C). This means that the α side of the hexose, but not the β side, is exposed on the outside of the monolayer, as seen from the crystal packing. The corresponding non-binding glycolipid which differs only in having a non-hydroxy fatty acid as the hydrophobic part instead of a 2-hydroxy fatty acid has been studied by NMR spectroscopy (see reference 32) which shows that the hexose is placed perpendicularly to the plane of the monolayer, and thus rotated around $C_1$–$C_2$ of the long-chain base. Although the studies were performed by separate methods applied to separate molecules, they establish the preferred conformations which differ in a way which is relevant in the present context. Similar to the dense intermolecular packing in the crystal, ceramide structures show a self-condensation effect in a monolayer on water (and probably also the biological membrane) which is due to intermolecular hydrogen bonding (see reference 33). For the closely packed glycolipids compared, this means that the non-hydroxy fatty acid species presents neither the α nor the β side of the hexose for binding in contrast to the 2-hydroxy fatty acid-containing species. From this, it may be concluded that the α side of the hexose is involved in the binding of the virus and that the 2-hydroxy group is critical for making this side accessible for binding.

A second factor which is important for receptor epitope designation is the nature of the protein on the virus which most probably binds this receptor. For instance Sendai virus (belonging to the paramyxo virus group and used extensively for experimentation) has two proteins on its surface (see reference 2 and 3). The HN (hemagglutinin-neuraminidase) protein carries the binding site for the first-step receptor containing neuraminic acid. The second protein, the F (fusion) protein, has been shown to be essential for the fusion of the viral membrane with the host cell plasma membrane (penetration), which fusion is necessary for delivery of the viral nucleocapside to the cytoplasm (see reference 2 and 3). The involvement of the highly conserved N-terminal hydrophobic peptide sequence of the F protein in this process has recently been substantiated by inhibition with a series of synthetic peptides similar to the natural sequence (see reference 35). Analogous N-terminal peptides exist on the surface of other viruses (see reference 2, White et al.). The material presented in reference 35 shows that the site of action of these synthetic peptides is on the target cell and that the effect is saturable, indicating receptor sites of about $10^6$ per cell. The second-step receptor as defined herein should be identical with these sites since there are only two proteins on the Sendai virus surface and two binding properties. The most potent inhibitory synthetic peptide is the N-carbobenzoxy peptide Z-D-Phe-L-Phe-Gly (Z denotes carbobenzoxy). The N-terminal sequence of the virus surface protein is L-Phe-L-Phe-Gly. The unnatural carbobenzoxy group increases the effect about $10^3$ times compared to the peptide without this group. The unnatural D isomer is 500 times more potent than the corresponding L isomer.

These two sets of information, the crystal conformation of the receptor glycolipid and the structure of the inhibitory peptides most likely interacting with this receptor, have been used for molecular modelling of probable associations of peptide and receptor. Based on the logical assumption that the N-terminal part of the peptide should be closest to the bilayer, the optimal fit of the synthetic peptide mentioned above and the receptor conformation may be defined as follows. It should be noted that the nomenclature used to denote the position of atoms or functional groups in the molecule is according to reference 38.

1. Hydrophobic interaction between the benzoxy group of the peptide and the paraffin chains of the receptor fatty acid and long-chain base.

2. Hydrogen bonds between N of D-Phe and C=O of the fatty acid and OH3 of the base and C=O of D-Phe.

3. Hydrophobic interaction between the benzene ring of D-Phe and the α side of the hexose and $CH_21$ of the base, including CH1, CH3 and CH5 of the hexose ring. It is obvious that a replacement of D-Phe with the natural L-Phe does not allow such an intimate association.

4. The benzene ring of L-Phe of the synthetic peptide may interact hydrophobically with the paraffin chains of this and adjoined receptor molecules. Thus, a hydrophobic interaction is satisfied for all three benzene rings.

The curves from quantitative binding assays (see below) indicate a low-affinity binding of the natural receptor to individual sites on the virus, needing multivalency for efficient binding. This explains why the synthetic soluble univalent peptide with the natural sequence is of low potency for inhibition. The role of the unnatural N-carbobenzoxy group is to improve the binding by additional hydrophobic interaction with the receptor compared to the natural structure. This group and the better steric fit with the unnatural D-Phe than L-Phe are not needed in case of a multivalent binding through the natural peptide of the intact virus particle, providing a sufficiently strong total interaction. This may indicate that the hydrophobic receptor part interacting with the carbobenzoxy group is not functional for the virus. However, it is anticipated that an established interaction between virus and a host cell membrane may include a further hydrophobic area than defined by the epitope as outlined above, after a primary interaction and breaking of the membrane resistance has been effected.

Viruses known to carry hydrophoic N-terminal peptides show a slight variation in the sequence although hydrophobicity is required. Also, there are different effects of inhibition for separate viruses using various synthetic N-carbobenzoxy peptides, with a relative reversal of potency in some cases (see reference 35). Extended molecular modelling shows that this "wobbling" in peptide structure is tolerated and produces a good interaction with the receptor. It should be realized that the binding to the receptor, according to this concept, is mediated by a linear peptide and not by a pocket formed by several peptide loops, often producing both a higher specificity and less tolerance to amino acid substitutions. On the other hand, a linear peptide is probably more efficient in gaining access to this partially buried epitope.

Based on the conformation of the natural second-step receptor, the specifications of a binding epitope carried by the compound to be used according to the invention may be outlined by comparison to similar parts on the natural epitope.

A. The α side of the hexose (Galβ or Glcβ) and C1 of the long-chain base

This is the "hydrophobic" side of the sugar with hydrophobic interaction sites at CH1, CH3, CH4 and CH5 of Gal and CH1, CH3 and CH5 of Glc. Also, $CH_2 1$ of the long-chain base represents hydrophobicity. Gal and Glc bind more or less equally well, showing that the stereochemistry at C4 is not essential. Furthermore, substitution at C4 does not block the binding but makes it weaker. These are the only known hexoses of monoglycosyl ceramides on the mammalian cell. The corresponding part on a synthetic epitope analogue may be comprised of a $C_5$-$C_7$ monosaccharide with similar characteristics on the α side of the hexose ring. This may be substituted in position 4 with a saccharide or another substituent which does not interfere sterically with the access to the binding epitope. Molecular modelling (see reference 38) of probable conformations of any such saccharide extensions shows that the substitutions that block the binding protrude from the same side as the α side of Glc while the substitutions allowing a binding protrude in other directions. This indicates a steric specificity in the approach from the virus and supports the statement that the α side is involved in the binding. In principle, the polar/hydrophobic part may in fact be any cyclic structure which carries the traits of the α side of Gal or Glc, i.e. a mainly hydrophobic ring part with extending polar substitutions in the form of, e.g., OH, SH or =O. Some of these substitutions may be non-polar in the form of, e.g., halogen, $CH_3$, a shorter alkane or alkene, to optimize the balance between hydrophobic and polar residues.

B. Hydrogen bonding sites at C=O of fatty acid (bond acceptor) and OH3 of the base (bond donor and acceptor)

OH4 of phytosphingosine is not essential. OH2 of the fatty acid appears to be essential for the conformation of the receptor but not for direct interaction with the virus. As noted above, however, an established interaction after the primary specific epitope recognition may also make use of this OH for hydrogen bonding. The two bonding sites may be placed about 5–6 Å apart, and they may primarily be C=O, O=S=O, OH or NH.

C. The hydrophobic part

Based on the molecular modelling, this should include up to C6 of the acid and C8 of the base. However, as noted above, the natural peptide has only one interaction while the unnatural peptide also binds hydrophobically with the N-carbobenzoxy group, making a precise definition uncertain. Again, an established interaction between virus and cell membrane may, after primary epitope recognition and hydrogen bond-breaking of membrane resistance, include an extended hydrophobic interaction between peptide and membrane. This essential hydrophobic part may therefore vary and has no structural specificity. In a synthetic epitope analogue, the hydrophobic part may consist of a saturated or unsaturated, branched or linear, open-chain or cyclic hydrocarbon, or a combination thereof with a surface area of at least about 50–80 Å$^2$. A sufficient hydrophobicity may, however, also be created by the hydrophobic side of a rigid oligomer such as a short chain of polystyrene, polyethylene, polyvinyl, etc.

The dimensions of the natural epitope which may be concluded from the crystal conformation (see reference 31) are as follows: the hydrogen bonding sites of part B are situated about 6–8 Å from the centre of the hexose ring of part A. Part C is about 6–8 Å and about 8–10 Å broad. The total length of the binding epitope is therefore on the order of about 16–20 Å. A synthetic epitope analogue should therefore have dimensions of the same or approximately the same size.

As indicated above, the monosaccharide forming the polar/hydrophobic part of the epitope may be a pentose, hexose or heptose. such as naturally occurring monosaccharides, e.g. xylose, arabinose, glucose, galactose, fucose, ribose, tallose and mannose, or derivatives thereof such as deoxy sugars, acetylated or alkylated sugars, branched sugars, amino sugars and uronic acids. In order to possess the desired characteristics with respect to conformation in particular, the monosaccharide should preferably be in ring (such as furanose or pyranose) form. Suitable examples of such a monosaccharide are xylopyranose, arabinopyranose, glucopyranose, galactopyranose, mannopyranose, etc. As further indicated above, this monosaccharide may be substituted at a position where the substituent does not interfere sterically with the binding. For most monosaccharides, this means that the substitution may occur at position 4 (carbon atom 4 of the heterocyclic ring). In principle, the substituent may be any substituent which fulfils the above criterion and which furthermore does not disturb the balance between polarity and hydrophobicity in this part of the epitope. Preferred substituents are mono-, di-, tri-or tetrasaccharides such as Gal, Glc, Xyl, Ara, Fuc, Rib, Man, Man-α1→3Man, Manα1→2Man, Manα1→6Man, Galβ1→2Man, Fucα1→2Gal, Fucα1→3-Gal, Fucα1→6Gal, Galβ1→2Gal, Galβ1→6Gal, Galβ1→3Gal, Galα1→3Galβ, Galα1→4Galβ, Glcα1→4Glc, Glcβ1→4Glc, Glcα1→4Glcβ1→4Glc, Glcα1→4Glcα-1→4Glc, Galβ1→3Galβ1→4Glc, Galβ1→3Galβ1→3Galβ1→4Glc, Glcα1→6Glcα1→4-Glcα1→4Glc, Galα1→3(Fucα1→2)Galβ, any suitable combination thereof or a derivative thereof such as a suitably acetylated, alkylated, branched or aminated derivative thereof (the abbreviations used are in accordance with accepted carbohydrate nomenclature).

The three parts constituting a synthetic binding epitope analogous to the natural binding epitope should be joined to present a total binding epitope of the indicated dimensions and with the characteristics described above exposed on the same side of the designed surface. This may be achieved by synthesis of a rather rigid epitope similar to the natural epitope. Thus, the link between the polar/hydrophobic part and the polar part may comprise two suitably substituted carbon atoms with the conformation of the natural binding epitope. Furthermore, the link between the polar/hydrophobic part and the polar part may be established by a linkage between glycosidic oxygen or glycosidic sulphur or an ether or thioether on the polar/hydrophobic part and a $CH_2$ group, or a similar group, on the polar part. If the coupling between the polar/hydrophobic part and the polar part is to be short and rather rigid, the glycosidic linkage is of β anomerity. However, the three parts may also be joined more flexibly to each other provided that the nature and length of the link does not interfere with the adoption of the binding surface of the three parts with the dimensions outlined above. Provided this criterion is satisfied, the specifications of A in particular may be more varied; if used, the anomeric linkage may for instance be of the α type.

As indicated above, receptors on target cells are most often either glycoproteins or glycolipids. As appears from the conformation specifications for the natural receptor, however, it has been found that, in nature, only glycolipids may function as second-step receptors for virus binding. The present invention is therefore primarily concerned with the use as antiviral agents of lipid-linked carbohydrates, including glycolipids, glycosphingolipids and glycoglycerolipids, or receptor-active analogues thereof. Examples of glycolipids useful for this purpose are D-galactopyranosyl-β-diglyceride or D-galactopyranosyl-α1→6-D-galactopyranosyl-β-diglyceride, which, in nature, may be found on the surface of plant cell membranes and have been found to possess the properties of the second-step binding receptor, indicating their usefulness in combating plant diseases of viral origin.

The intermediate zone of glycoglycerolipids shows hydrogen bond acceptors only and therefore does not cause the tight molecular packing and highly self-condensing monolayer which have been indicated to be important causes of the proper conformation and presentation of the binding epitope in the case of glycosphingolipids. Experiments have shown that the binding to glycoglycerolipids does not require a 2-hydroxy fatty acid, as the binding epitope is available to the virus even in the absence of 2-hydroxy fatty acid due to the more spaced presentation of the glycoglycerolipid molecules. Where glycosphingolipids are concerned, it is preferred that the hydrophobic part comprises a 2-hydroxy fatty acid as this has been shown to cause a more efficient binding. Accordingly, the compound to be used as an antiviral agent may be a sphingosine-2-D-hydroxy fatty acid of the general formula I or a phytosphingosine-2-D-hydroxy fatty acid of the general formula II or a dihydrosphingosine-2-D-hydroxy fatty acid of the general formula III $$\begin{array}{c} \text{O} \quad \text{OH} \\ \| \quad | \\ \text{HN}-\text{C}-\text{CH}-R_3-R_1 \\ | \\ \text{ROCH}_2\text{CH} \\ | \\ \text{HO}-\text{CH}-\text{CH}=\text{CH}-R_3-R_2 \end{array} \quad \text{I}$$

or $$\begin{array}{c} \text{O} \quad \text{OH} \\ \| \quad | \\ \text{HN}-\text{C}-\text{CH}-R_3-R_1 \\ | \\ \text{ROCH}_2\text{CH} \quad \text{OH} \\ | \qquad | \\ \text{HO}-\text{CH}-\text{CH}-\text{CH}_2-R_3-R_2 \end{array} \quad \text{II}$$

or $$\begin{array}{c} \text{O} \quad \text{OH} \\ \| \quad | \\ \text{HN}-\text{C}-\text{CH}-R_3-R_1 \\ | \\ \text{ROCH}_2\text{CH} \\ | \\ \text{HO}-\text{CH}-\text{CH}_2-\text{CH}_2-R_3-R_2 \end{array} \quad \text{III}$$

wherein R represents a saccharide with the conformation of β-galactopyranose, at least in the receptor-active part, and $R_1$ and $R_2$ each independently represent a methyl group, or a CHO, $NO_2$, $NH_2$, OH, SH, $CONHNH_2$, $CON_3$ or COOH group. When the receptor or receptor analogue is to be used as such, i.e. is efficient enough to effect binding in itself, $R_1$ and $R_2$ are preferably methyl, but when the natural epitope or the synthetic epitope analogue are to be presented in a multivalent form (see below), it is preferred that $R_1$ and/or $R_2$ represents a reactive group which is capable of either interacting with similar groups on the receptors themselves or reacting with similar groups on a carrier. $R_3$ represents a hydrocarbon moiety which may comprise a linear or branched, saturated or unsaturated hydrocarbon with a chain length of at least 5 carbon atoms. However, the hydrocarbon chains are most usually linear and saturated or monounsaturated. R may be a monosaccharide as specified above, optionally substituted in position 4 by one or more other saccharides as mentioned above; thus, the total saccharide comprising the polar/hydrophobic part may for instance be
Galβ,
Glcβ,
Galβ1→4Glcβ,
Galα1→4Galβ,
Galα1→3Galβ1→4Glcβ,
Galα1→4Galβ1→4Glcβ,
Fucα1→2Galβ1→4Glcβ,
GlcNAcβ1→3Galβ1→4Glcβ,
GalNAcβ1→4Galβ1→4Glcβ,
Galα1→3(Fucα1→2)Galβ1→4Glcβ,
Galβ1→3GlcNAcβ1→3Galβ1→4Glcβ,
Galβ1→4GlcNAcβ1→3Galβ1→4Glcβ,
Galβ1→3(Fucα1→4)GlcNAcβ1→3Galβ1→4Glcβ, or
Galβ1→4(Fucα1→3)GlcNAcβ1→3Galβ1→4Glcβ,
wherein the term "NAc" denotes an N-acetylation of the saccharide.

It has been experimentally established that glycolipids with up to five saccharides are able to bind the viruses; a larger oligosaccharide is likely to constitute a steric hindrance in the access of the virus to the epitope.

The best natural binders, as established by quantitative binding studies (see below), have been found to be Glcβ Cer and Galβ Cer. This indicates that the use of more than one saccharide is superfluous for binding purposes although it may be necessary from the point of view of the availability of starting materials in the preparation of the receptors or receptor analogues, etc.

As repeatedly indicated above, the use according to the invention also extends to receptor-active analogues of the natural binding epitope. Such analogues may, of course, have any form provided that they meet the requirements with respect to conformation described above, and such analogues may therefore be selected from a wide variety of compounds. It has, however, been found that compounds of the general formula IV

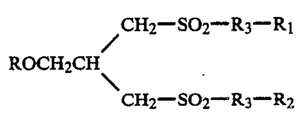

IV wherein R, $R_1$, $R_2$ and $R_3$ are as defined above, form a particularly interesting group of receptor analogues to be employed for the present purpose. In the case of the synthetic receptor analogues, the same saccharides as those listed above for natural receptor substances may be employed. Particularly interesting compounds of this general formula are 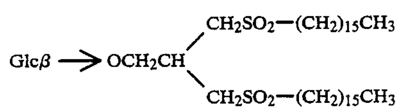 and 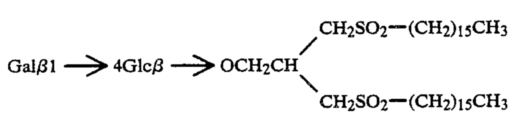 which have been found to show an avidity of binding which is on the same order of magnitude as that of the natural receptor substances (cf. Example 5).

As these receptor analogues have been found to be comparable to the natural substances with respect to properties and conformation (dimensions), they are fully valid as substitutes for the natural receptor. The advantage of using these or similar synthetic receptor analogues lies in the method of their preparation which may be effected by simpler means than if the natural receptor were to be produced either synthetically or by the more cumbersome method of harvesting them from cell surface membranes.

The synthetic receptor analogues of the general formula IV may be prepared by a process comprising reacting a glycoside of the general formula V

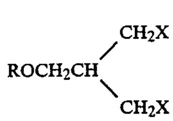

V wherein X represents a leaving group and R is as defined above, with a thiol of the general formula VI $$HS—R_3—R_1 \qquad VI$$

wherein $R_3$ and $R_1$ are as defined above and reacting the product with an oxidising agent. The reaction may be carried out in water or a suitable organic solvent such as ethyl acetate, methylene chloride, ether and dimethyl sulfoxide. The reaction may suitably be carried out at room temperature. The reaction time may be from 24 to 48 hours. The reaction is generally carried out with slightly more than 2 equivalents of the thiol of the general formula VI to one equivalent of the glycoside of the general formula V. The reaction may be carried out under slightly alkaline conditions, and the saccharide may be suitably protected.

The oxidation of the resulting thio compounds to the corresponding sulphones of the general formula IV may take place using four equivalents or more of the oxidizing agent. Examples of useful oxidizing agents are peracids such as m-chloroperbenzoic acid, peroxides such as tert.butyl hydroperoxide, aminooxides, gaseous oxygen or inorganic oxidizing agents such as potassium permanganate, chromium trioxide, etc. The reaction is usually carried out at room temperature.

Another interesting group of compounds are compounds of the general formula VII $$ROCH_2CH_2SO_2—R_3—R_1 \qquad VII$$

wherein R, $R_1$ and $R_3$ are as defined above. These compounds may be prepared from the corresponding sulfides by oxidation as described above.

In order to be useful as a diagnostic, prophylactic or therapeutic agent in connection with viral infections, it is important that the compound used for these purposes is provided in such a form or in such a way that a sufficient affinity for the virus is obtained. Thus, the compound, if sufficiently active, may be provided as such in water-soluble form, i.e. in univalent form (that is, appearing as discrete units of the compound each carrying substantially only one binding epitope). This form is expected to be particularly relevant where synthetic receptors are concerned as these may have a far greater affinity for the viruses than the natural receptors which have been found to show a low-affinity binding. Where the natural and, supposedly, several of the synthetic receptors are concerned, the compound may therefore usually preferably be provided in such a form that it presents multiple binding sites for the virus (in the following termed "multivalent binding") in order to produce an efficient binding. In nature, multivalent binding is effected by a large number of protein molecules on the virus surface and a corresponding number of glycolipid receptors on the host cell. When used for the present purpose, the compound should therefore be provided in a form that mimics this multivalent binding. This may be achieved by the use of the natural glycolipid receptors or synthetic receptor analogues of a similar size which may be presented as micelles or on hydrophobic surfaces (to resemble the target cell surface). However, the less stable micelles may give rise to unspecific binding to any surface, and therefore the presentation of the receptor or receptor analogue on a solid phase is preferred.

Alternatively, the compound may be multivalently coupled to a macromolecular carrier which may be either of two types: one in which the carrier has a hydrophobic surface to which a hydrophobic part of the compound is associated by hydrophobic non-covalent interaction, the hydrophobic surface for instance being a polymer such as a plastic or any other polymer to which hydrophobic groups have been linked, such as polystyrene, polyethylene, polyvinyl, etc., or it may be a macromolecular carrier to which the compound is covalently bound. In this latter instance, a suitable carrier may be a natural or synthetic polymer. Thus, the carrier may be an oligo- or polysaccharide, e.g., cellulose, starch, glycogen, chitosane or aminated sepharose, to which the receptor or receptor analogue may be bonded through a reactive group on the hydrophobic part, such as a hydroxy or amino group present on the receptor-active substance, an oligo- or polypeptide such as a globulin, albumin, fibrin, etc., the bond being provided through, for instance, a hydroxy or amino group on the hydrophobic part of the receptor or receptor analogue, a combination thereof or a similar suitably substituted conjugate. The carrier may also be an inorganic carrier such as a silicon oxide material, e.g. silica gel, zeolite, diatomaceous earth, or the surface of various glass types such as aminated glass to which the receptor or receptor analogue may be bonded through a hydroxy, carboxy or amino group on the hydrocarbon moiety of the receptor-active substance. When the compound is to be used for prophylaxis or therapy, it is vital that the carrier is a physiologically and pharmaceutically acceptable carrier, such as a non-toxic and/or non-allergenic carrier. Carriers of this type which are at present contemplated to be useful for this purpose are, for instance, poly-L-lysine and poly-D,L-alanine.

The present invention is based on the finding that viruses in general appear to need the second-step receptor for the essential penetration into the host cell cytoplasm so that the natural binding epitope or a synthetic epitope analogue in uni- or multivalent form may be employed to prevent viral infection by blocking the available binding sites on the virus so as to inhibit invasion of the virus into epithelial cells at the port-of-entry of viral infections. Examples of such ports-of-entry are the mucous membranes of the eye, nose, oral cavity, throat, respiratory tract, gastrointestinal tract, urinary tract and reproductive organs. The general applicability of the present invention is based on the fact that compounds corresponding to or analogous to the second-step binding receptor found on target cells have been shown to bind a wide variety of viruses belonging to the families Adenoviridae, Herpetoviridae, Orthomyxoviridae, Paramyxoviridae, Rhabdoviridae, Reoviridae. Other virus families of interest in this connection are the Picornaviridae and Retroviridae. Thus, the viruses of interest include both DNA and RNA viruses and particles with and without a bilayer membrane envelope, which viruses are the cause of a wide range of diseases affecting many different organ systems, examples of which are various influenzas and common colds, diarrhoeas, herpes I and II, mumps, measles, rabies, AIDS, leukaemia, etc.

Prophylaxis in the animal, including human, system may be obtained by direct application on the mucous membrane of interest of the virus-inhibiting compound in a pharmaceutically acceptable form such as a suspension, aerosol, ointment, suppository, spray, lotion or solution containing the receptor or receptor analogue in univalent or multivalent form as described above. There, the active substance binds the virus and blocks the binding site for the second-step receptor. Prophylaxis may also be effected by exposing the virus particles secreted from infected patients or animals to a compound of the invention applied on the surface of apparatus, objects or surfaces which may be or have been brought in contact with such secretions, i.e. the compounds may be used as disinfectants. Exposure of the virus to a multivalent receptor may not only prevent the viruses from penetrating into the target cell, but may also agglutinate the virus particles through multivalent attachments. This means that most virus particles will also be prevented from attachment to the first-step receptor. Prophylaxis in the plant system may for instance be effected by spraying seeds, seedlings or adult plants with an effective dosage of a receptor or receptor analogue formulated in a manner to facilitate application such as a solution, suspension or emulsion of a receptor or receptor analogue in multivalent or univalent form as described above.

The use according to the invention may also comprise a therapeutic use in cases where infection has already taken place, i.e. when the virus has already passed the mucous membrane at the port-of-entry and settled within the organism. Therapeutic administration of the receptor is at present contemplated to be achievable by injection or through intestinal absorption or direct absorption from other mucous membranes of a soluble low-molecular weight univalent receptor analogue with increased virus binding potency as outlined above. Thus, the injected or absorbed substance is expected to bind virus particles that are budding (being expelled) after multiplication in infected cells and prevent them from entering new cells (spread of infection). A similar prevention of spread is also useful in, for instance, the small intestine after virus infection by oral presentation on a multivalent carrier, e.g. as tablets or capsules in acid resistant form. As an example of application after absorption may be mentioned rabies infection where, after a bite (wound), the virus travels through the nerve pathways to finally reach the central nervous system (after a period of several months or even years) to produce the lethal effect. A compound as described above made to penetrate the blood-brain barrier or injected directly into the cerebro-spinal fluid is expected to prevent the brain damage caused by viral multiplication within nerve cells.

The dosages in which the receptors or receptor analogues are administered may vary widely depending on the intended use, whether for prophylaxis, including disinfection, or therapy, the type of infection to be combated, the age and condition of the patient, etc., but is expected to be at a milligram level. For rotavirus infection (diarrhoea), a daily dose of 1 µg receptor per human individual has been calculated to agglutinate/inactivate all viruses produced during one day, provided the receptor is bivalent and only one bivalent receptor is used per virus particle. In practice, of course, a far larger dosage is needed to secure an effective binding of all the virus particles present. Contrary to what is the case with most medicaments now in use, the dosage level may not be so essential as the toxic effects of the receptor or receptor analogues are expected to be negligible since, in fact, at least the natural receptors are substances which are present in large amounts in the human or animal system.

The use according to the invention may furthermore be a diagnostic use, utilizing the knowledge of the second-step receptor function with respect to the binding of viruses. For diagnostic purposes, virus particles present in secretions from infected patients or other samples to be tested may be exposed to the receptor substance which may be presented on the surface of an appropriate carrier material in the form of, for instance, dipsticks, immunological test cards, polymeric beads or the like. After binding, the surface is carefully washed, and the presence of the virus may be shown in several ways already established within clinical virology. For instance, the virus may first be adsorbed in microtiter wells followed by detection by ELISA methods (see reference 1, Materials and Methods and Example 6). Also, the other assays developed by the present inventors may be adapted for a simplified diagnostic use.

It is also contemplated that the compounds described above may be used for various biotechnological purposes such as the preparation and isolation of virus particles or virus surface components through the use of established affinity chromatographic methods. For this purpose, the receptor substance may be coupled to a solid support such as multivalently coupled to a macromolecular carrier as described above for binding the ligand in chromatographic columns, for electrophoresis, filtration, sedimentation or centrifugation. The properties of the receptor (binding constant, etc.) may be optimized for elution, etc., by the design of the synthesis of the compound so as to avoid irreversible binding of the virus to the receptor. In this way, it may be possible to isolate or purify virus particles or virus substances and/or detect viruses in various samples by their binding to receptor or receptor analogues coupled to these solid supports.

Another suggested use of the receptors or receptor analogues may be to isolate the substance on the virus membrane which is responsible for virus binding. It is contemplated that this substance may be used for vaccination purposes, i.e. to immunize the human being or animal in question not only against the viral disease imparted by the viral species from which the substance has been derived, but also against other viral diseases imparted by viruses having the same substance on their surface. Thus, it is at present assumed that a broadspectered vaccine against a variety of viral diseases may be produced in this manner. Compared to the usual methods of vaccination using attenuated virus preparations, such a vaccine would have the decided advantage that non-infectous virus components may stimulate the production of antibodies which are able to neutralize the virus in question by blocking the essential molecule for virus entry into the host cell for infection.

Finally, it is contemplated that it may be possible to select binding proteins or glycoproteins from the viruses in the manner described above which may be used for targeting drugs to specific cells within an organism. For instance, a liposome (lipid vesicle) may be equipped with, e.g., a monoclonal antibody with specificity for a certain target cell (for instance a tumor cell or a cell carrying intracellular parasites). To avoid being eventually inactivated through endocytotic uptake to the lysosomes, the liposome may also be tagged with the viral component recognizing the second-step receptor. In this way, the established virus mechanism for penetration may be employed as part of a vehicle for carrying a toxic drug. The liposome may be exchanged with a direct chemical coupling of antibody (first-step) and viral component (second-step) with the active subunit of a bacterial toxin exerting its actions only inside the cell (see reference 12).

The present invention also relates to an antiviral agent which is a compound with the characteristics and properties described above. It is to be understood that this aspect relates to the compound in isolated form, that is, it does not include the compound when carried by the cells which, in nature, carry the compound.

The present invention further relates to a pharmaceutical composition which comprises a compound with the characteristics and properties described above which has been formulated together with a pharmaceutically acceptable vehicle or excipient.

The composition may be formulated for administration by any suitable route such as by oral ingestion, injection or topical application. Thus, the composition may be in the form of, for instance, a suspension, solution, aerosol, ointment, lotion, cream, spray, suppository, implant, tablet, capsule or lozenge containing the receptor or receptor analogue in univalent or multivalent form as explained above. It is contemplated that for prophylactic use, the composition may be in a form suitable for topical application on the mucous membrane of, e.g., the eye, nose, oral cavity and throat, such as an aerosol, spray, lozenge, lotion or cream, and for the purposes of disinfection, the receptor or receptor analogue in question may be provided as, e.g., paper tissues or a liquid which is suited for rinsing apparatus, objects or surfaces which may be or has been brought into contact with secretions from infected patients.

For therapeutic applications, it is contemplated that compositions adapted for injection, such as solutions or suspensions of the receptor or receptor analogue in a suitable vehicle such as water or isotonic saline, as well as adapted for oral ingestion (and absorption through the intestinal mucosa) such as tablets or capsules will be convenient. In order to protect the receptor or receptor analogue from possible impairment or degradation in gastric juices, the tablets or capsules may be provided with an acid-resistant coating. Compositions adapted for absorption of the receptor substance through mucous membranes may also be in the form of suppositories such as vaginal or rectal suppositories.

The pharmaceutically acceptable vehicles or excipients and optionally other pharmaceutically acceptable materials present in the composition such as diluents, binders, colorants, flavouring agents, preservatives and disintegrants are all selected in accordance with conventional pharmaceutical practice in a manner understood by persons skilled in the art of formulating pharmaceuticals.

DESCRIPTION OF THE DRAWING

The invention is further described with reference to the drawing in which

FIG. 8 shows the structural concept of the outer monolayer of the animal cell surface membrane as described in detail elsewhere (Karlsson, in Chapman, ed., *Biological Membranes*, Vol. 4, Academic Press, London, 1982, pp. 1-74). The three major lipid components are sphingolipid, glycerolipid and cholesterol, and in the intermediate zone they carry a number of hydrogen bond acceptors and donors which create a system of intermolecular laterally oriented hydrogen bonds of importance for membrane stability. Binding sites are especially dense in epithelial cells of mucous membranes, the port-of-entry of viral infections. As shown in Example 4, epithelial cells are abundant in the second-step receptor (substance 1 and 2 of Table 3), which is a sphingolipid containing both hydrogen bond acceptors and donors. Plant cells also contain substance 2 of Table 3 in addition to substances 26 and 27 of Table 3, which are glycerolipids. These bind the viruses (Table 3). Viruses have therefore developed a property (through a surface peptide) which is able to utilize, for selective binding, all three parts of the surface membrane that are essential to make the membrane a stable barrier. In this way, the second-step receptor for virus penetration and infection is a normal component of all cell surfaces.

MATERIALS AND METHODS

Figure 1:
FIG. 1 shows an assay of Sendai virus (S variant) binding to the first-step receptor, analyzed as described in Materials and Methods. The two lanes to the left have been detected chemically and are total gangliosides (neuraminic acid-containing glycolipids) of human erythrocytes (lane 1) and human brain (lane 2). The same two lanes are shown to the right after binding of Sendai virus and autoradiography. As shown, there is no virus binding to the major brain bands of lane 2. In contrast, there is an apparently strong binding to several erythrocyte bands of lane 1, especially slow-moving ones.

Preparation and Structural Characterization of the Natural Receptor and Related Substances The human and animal glycolipid samples used for binding studies, either pure glycolipid species or total or partial glycolipid mixtures, were prepared substantially as described in reference 13 from lyophilized tissue through repeated chloroform-methanol extractions, mild alkaline treatment to degrade non-sphingolipids and dialysis for 4 days against water to remove water-soluble products. Remaining lipid material is first separated on a silica gel column to elute the dominating fatty acid esters before the totally alkali-stable sphingolipids. These are then separated on DEAE cellulose or DEAE Sepharose ® columns in a non-acid and acid glycolipid fraction. The acid fraction is then usually separated by gradient elution from DEAE Sepharose ®. The non-acid fraction is acetylated in acetic anhydride and pyridine and repeatedly fractionated on silica gel with stepwise or continuous gradient elution with methanol in chloroform or other solvents. Fractions are deacetylated in mild alkali and further fractionated until pure if necessary. Purity is tested by thin-layer chromatography and further checked by mass spectrometry and NMR spectroscopy as described below.

To prepare glycolipids completely free from non-glycolipid contaminants, 250 ml of methanol are added to about 250 ml of human blood plasma of one transfusion unit, and the mixture is heated to 70° C. for 30 minutes with constant stirring in a one-liter evaporation bottle. The extract is filtered and the residue transferred back to the extraction bottle. The procedure is repeated twice with 250 ml of chloroform/methanol 2:1 (by volume) and once with 250 ml of methanol. The combined extracts are evaporated to dryness with the addition of small volumes of toluene.

Small amounts of wet cells may be extracted in a similar way. On a larger scale, the tissue is first lyophilized in pieces and subjected to extraction in two steps in a Soxhlet apparatus. In the case of human small intestine (e.g. 130 g dry weight), the first extraction is with chloroform/methanol 2:1 (by volume) for 24 hours (1000 ml of solvent in a 2000 ml round bottle placed in an asbestos-insulated electrical heating device). The second extraction is carried out with 1500 ml of chloroform/methanol 1:9 (by volume) for 24 hours. The combined extracts are evaporated to dryness without filtration.

The dried plasma extract residue is treated with 50 ml of 0.2M KOH in methanol for 3 hours in a bottle containing five glass beads for fine dispersion during occasional shaking. The KOH is neutralized with 1 ml of acetic acid. The mixture is dialyzed against water in a dialysis bag after the addition of 100 ml of chloroform and 40 ml of water to produce a two-phase system. After dialysis for 4 days against running tap water, the content of the bag is evaporated at 70° C. with repeated additions of toluene. The sample is finally filtrated and eluted with chloroform/methanol 2:1 (by volume) and methanol. In case of the intestinal total extract, 500 ml of KOH in methanol are used.

The plasma sample (about 1.4 g) is loaded on a 10 g column of silica gel packed in chloroform. The silica gel used is principally obtained from Mallinckrodt Chem. Works, St. Louis, U.S.A., sieved to a particle size of more than 45 μm and dried. However, LiChroprep Si 60 (E. Merck, Darmstadt, West Germany) with comparable specifications has similar properties although some of the silica gel may elute. Three fractions are eluted: 100 ml of chloroform elute the main bulk (about 1 g of the extract (cholesterol and methyl esters of fatty acids); 100 ml of chloroform/methanol 98:2 (by volume) may contain free ceramide; 100 ml of chloroform/methanol 1:3 (by volume) and 100 ml of methanol elute all glycolipids and alkali-stable phospholipids (about 60 mg). In case of the dialyzed small intestinal sample (about 40 g), 50 g of silica gel and 500 ml of solvent are used in each step.

The third fraction from the silica gel chromatography of the plasma sample is loaded on a column of 5 g of DEAE cellulose (DE-23, Whatman) in acetate form packed in chloroform/methanol 2:1 (by volume). The loaded sample is allowed to equilibrate on the column for 1 or 2 days. Two fractions are eluted, one with 100 ml of chloroform/methanol 2:1 (by volume) and 100 ml of methanol eluting non-acid glycolipids and alkali-stable phospholipids, mainly sphingomyelin, and one with 50 ml of 5% (w/v) LiCl in methanol eluting acid glycolipids (sulphatides and gangliosides) and alkali-stable phospholipids. The latter fraction is dialyzed with 30 ml of chloroform and 20 ml of water against running tap water for 4 days. It may be used as a total acid glycolipid fraction or be further processed as described to separate sulphatides and gangliosides (Breimer et al., *J. Biochem.* 93, 1983, pp. 1473–1485). The first fraction is evaporated to dryness and acetylated. In case of the intestinal sample (about 2 g), 20 g of DEAE cellulose are used.

Acetylation of the dry non-acid plasma sample is performed in the dark overnight in 2 ml of chloroform, 2 ml of pyridine and 2 ml of acetic anhydride. The chloroform is added to improve solubility and ensure complete reaction. 5 ml of methanol and 5 ml of toluene are added, and the sample is evaporated in a stream of nitrogen on a heated water bath and finally subjected to vacuum suction.

The acetylated plasma sample is loaded on a 10 g column of silica gel packed in chloroform/methanol 98:2 (by volume). For this purpose, particles smaller than 45 μm treated with methanol and dried are used. Three fractions are eluted: 100 ml of chloroform/methanol 95:5 (by volume), 100 ml of chloroform/methanol 90:10 (by volume), and 100 ml of chloroform/methanol 1:3 (by volume) plus 100 ml of methanol. The third fraction contains mainly acetylated sphingomyelin. The first two fractions which contain acetylated glycolipids and some contaminants are evaporated together and deacetylated. For the intestinal fraction, 50 g of silica gel are used.

Deacetylation of acetylated glycolipids may be performed in two ways, one with and one without a dialysis step.

Method A. For the plasma sample, 2 ml of toluene, 2 ml of methanol and 4 ml of 0.2M KOH in methanol are used with occasional shaking during 30 minutes (for the intestinal sample, 5, 5 and 10 ml, respectively, are used). After addition of 0.5 ml of acetic acid, the sample is transferred with 10 ml of chloroform and 10 ml of water to a dialysis bag (two-phase system) and dialyzed for 4 days against running tap water. The content of the bag is evaporated at 70° C. with repeated additions of toluene.

Method B. In this case, no dialysis is needed since the amount of potassium acetate formed after neutralization is very low compared to the glycolipid. The reagent is composed of 1 ml of 0.2M KOH in methanol, 14 ml of methanol and 5 ml of toluene. Of this, 0.1 ml is used for up to 2 mg of acetylated glycolipid, 0.2 ml for up to 4 mg, 0.5 ml for up to 15 mg, 1 ml for up to 40 mg and so on. The sample to be deacetylated is evaporated to dryness, the appropriate amount of reagent is added and the mixture is intermittently agitated for 2 hours after which the KOH is neutralized with acetic acid and the solvents evaporated. As an example, deacetylation of 40 mg of acetylated glycolipid with 1 ml of reagent produces about 1 mg of potassium acetate remaining in the glycolipid sample. If necessary, potassium ions may be removed by filtration through e.g. chloroform/methanol-washed Amberlite ® CG-50 type I in H+ form (Rohm and Haas, Philadelphia, Pa., U.S.A.), and the deacetylation mixture without added acetic acid may be filtered directly. However, some irreversible adsorption of glycolipid may occur and eluted resin may also contaminate. It is therefore preferred that a certain amount of potassium acetate remains in the sample.

The deacetylated plasma sample is filtered through a column of 2 g of DEAE cellulose packed in chloroform/methanol 2:1 (by volume). The loaded sample is allowed to equilibrate for 1-2 days before elution with 50 ml of chloroform/methanol 2:1 (by volume) and 50 ml of methanol. The purpose of this step is to remove alkali-stable amino group-containing phospholipids which have been transferred into N-acetylated derivatives during the acetylation procedure. This makes them acid.

A final silica gel chromatography step removes nonpolar contaminants eluted in the first two fractions. The plasma sample is loaded on a column of 5 g of silica gel (particles smaller than 45 µm) packed in chloroform/methanol 98:2 (by volume). After elution of two fractions with each 50 ml of chloroform/methanol 98:2 (by volume), the pure glycolipids are eluted with 50 ml of chloroform/methanol 1:3 (by volume) and 50 ml of methanol. The final yield of total non-acid glycolipids in plasma from one transfusion unit of human blood is 6-8 mg.

The preparative steps are controlled by thin-layer chromatography (silica gel 60 nanoplates; E. Merck, Darmstadt, West Germany), preferably using chloroform/methanol/water 65:25:4 (by volume) for non-derivatized and chloroform/methanol 95:5 (by volume) for acetylated samples. Anisaldehyde is preferred as a detection reagent because it forms characteristic colours: glycolipids usually become green or blue-green, glycerophospholipids grey or violet, and sphingomyelin and ceramide blue (cf. reference 21).

The procedure outlined above results in a total non-acid glycolipid mixture (one to about 20 sugars) completely free from non-glycolipid contaminants. This fraction is important for testing the presence of the second-step receptor in various cell sources (see FIGS. 2 and 7). To isolate the second-step receptor in pure form from such glycolipid mixtures, the final silica gel chromatographic step described above may be slightly modified as follows. After elution with chloroform/methanol 98:2 (by volume), the one-sugar second-step receptor is easily eluted with chloroform/methanol 95:5-90:10 (by volume). For large-scale preparation from selected sources, the procedure described above may, however, be simplified a great deal as outlined below. Accessible second-step receptor sources may be mammalian intestine (see FIG. 7), yeast or fungi, and some invertebrates. For example, it has been shown that the starfish, Asterias rubens, which is easily available from the sea, is a rich source of the second-step receptor (substance 2 in Table 3, see Björkman et al., Biochim. Biophys. Acta 270, 1972, pp. 260-265). The mammalian brain is also a very rich source of the second-step receptor in the form of substance 1 in Table 3. For this purpose, lyophilized brain (e.g. bovine or porcine brain) is extracted with chloroform/methanol 2:1 (by volume) (at a volume which is 10 times the weight of the tissue) with gentle heating. The filtered extract is evaporated to dryness and reextracted with the same solvent and filtered. The evaporated extract is subjected to alkaline methanolysis overnight (limited volume, e.g. 500 ml for one brain, of 0.2M KOH in methanol). The mixture is then overneutralized with acetic acid to a pH of about 3.5 and solvent partitioned by adjusting the volumes to chloroform/methanol/water 8:4:3 (by volume). After standing overnight, the lower phase is evaporated to dryness and subjected to silica gel chromatography. This step is performed as a kind of filtration, using a short, broad column packed in pure chloroform and loaded with up to 1 g of extract per g of adsorbent. The major part of the extract is eluted with pure chloroform (cholesterol and methyl esters of fatty acids). The second-step receptor, Gal$\beta$Cer, is eluted with chloroform/methanol 95:5-90:10 (by volume). In the late elution phase, sulphated Gal$\beta$Cer may contaminate. To improve the yield of Gal$\beta$Cer, this mixture may be filtrated through DEAE cellulose, which binds the sulphated substance. If necessary, the last traces of pigmented substances may be removed by crystallization in ethanol. Precisely the same procedure may be applied to lyophilized starfish. In this case, cholesterol sulphate, and not sulphated Gal$\beta$Cer, is removed by DEAE cellulose.

Structural analysis of isolated fractions is done on non-degraded samples by mass spectrometry (see reference 14) and NMR spectroscopy (see reference 15) and a combined use of permethylated, permethylated LiAlH$_4$-reduced, and (in case of acid glycolipids) permethylated LiAlH$_4$-reduced trimethylsilylated derivatives. In this way, the sequence and anomerity of the oligosaccharide and the composition of the ceramide is obtained. Degradation is also performed to receive the information on the type of sugars and positions of linkage, through combined gas chromatography and mass spectrometry as described in reference 16.

Several synthetic ceramides were used, including the combinations sphingosine-non-hydroxy fatty acid, sphingosine-hydroxy fatty acid, phytosphingosine-non-hydroxy fatty acid and phytosphingosine-hydroxy fatty acid (see reference 17). Similar natural combinations of long-chain base and fatty acid were also prepared using the method referred to above. Sphingmyelin was obtained by the procedure described above. Various phosphoglycerides were prepared without alkaline degradation and separated on DEAE cellulose into acid (phosphatidylserine and phosphatidylinositol) and non-acid phospholipids. The non-acid phospholipids were then separated on silica gel columns into phosphatidylethanolamine and phosphatidylcholine. The substances were tested for purity by thin-layer chromatography and identified by analysis of components (see reference 18). Phosphatidylcholine, phosphatidylethanolamine and phosphatidylserine were also purchased from Sigma Chemical Co.

Two glycoglycerolipids of plant origin, galactosyldiglyceride and digalactosyldiglyceride, were purchased from Sigma Chemical Co.

Several synthetic monoglycosylceramides were received from Dr. Irmin Pascher, and their preparation has been described in Pascher, *Chem. Phys. Lipids* 12, 1974, pp. 303-315. These were galactopyranosylβ-and glucopyranosylβceramides with various combinations of long-chain base and fatty acid, such as sphingosine, dihydrosphingosine, phytosphingosine and 2-hydroxy and non-hydroxy fatty acids. One of these species, galactopyranosylβceramide with dihydrosphingosine and 2-D-hydroxyoctadecanoic acid, was determined in its crystal conformation (Pascher et al., *Chem. Phys. Lipids* 20, 1977, pp. 175-191) and was used to assign receptor binding epitope.

Figure 5A:
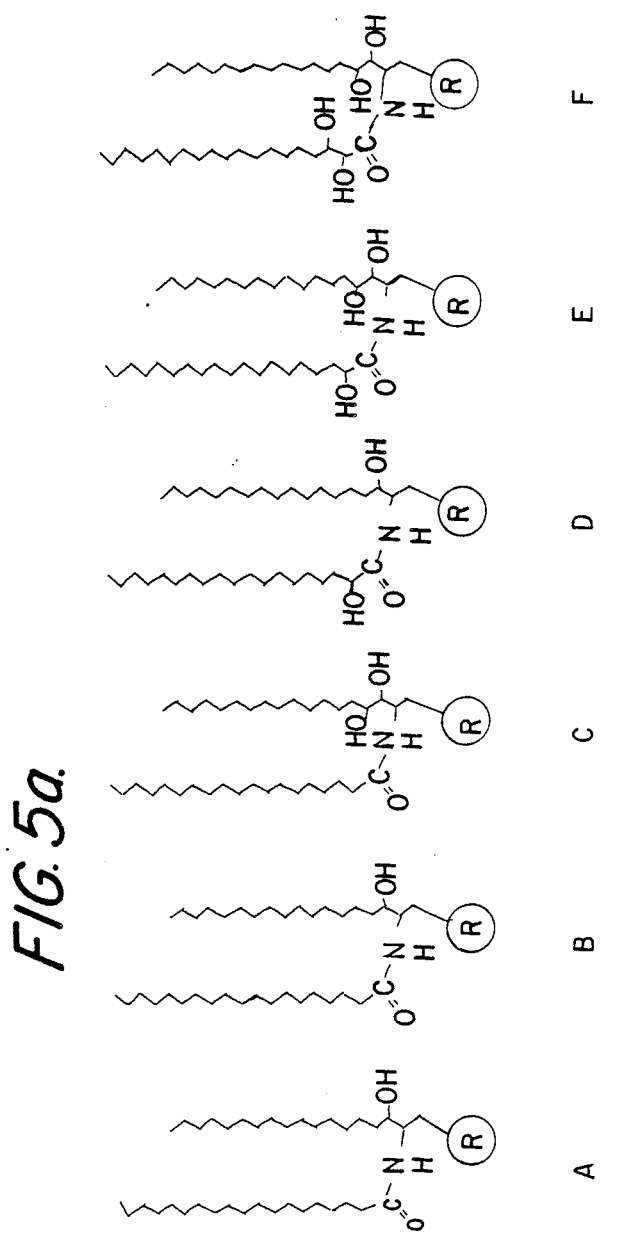
FIG. 5 shows examples of naturally occurring molecular species of ceramides (combinations of fatty acid and long-chain base). These have been summarized elsewhere (Karlsson, in Chapman, ed., *Biological Membranes*, Vol. 4, Academic Press, London, 1982, pp. 1-74). R includes the oxygen of C1 of the base and may be phosphorylcholine as in sphingomyelin or a saccharide as in glycosphingolipids. The major types of fatty acids are non-hydroxy, 2-D-hydroxy and 2-D,3-D-dihydroxy fatty acids with about 12-26 carbon atoms in the chain, which may be saturated, unsaturated, linear or branched. The major types of bases are dihydroxy (sphingosine, dihydrosphingosine and related bases) and trihydroxy bases (phytosphingosine and related bases). They have about 14-22 carbon atoms and the chain may be saturated, unsaturated, linear or branched. The absolute structures of the three classical bases are: Sphingosine: 1,3-D-dihydroxy-2-D-amino-4-trans-octadecene (of species B and D), dihydrosphingosine: 1,3-D-dihydroxy-2-D-aminooctadecane (of species A) and phytosphingosine: 1,3-D,4-D-trihydroxy-2-D-aminooctadecane (of species C, E and F). The most common species of mammalian cells are A-E, often with a 15-cis double bond in the fatty acid. The most common species of epithelial cells are D and E, which are the best virus binders (Table 4). Therefore, the viruses have selected, as second-step receptors, glycolipids with a ceramide composition which dominates in the epithelial cells, the port-of-entry of viral infections.
Figure 5B:
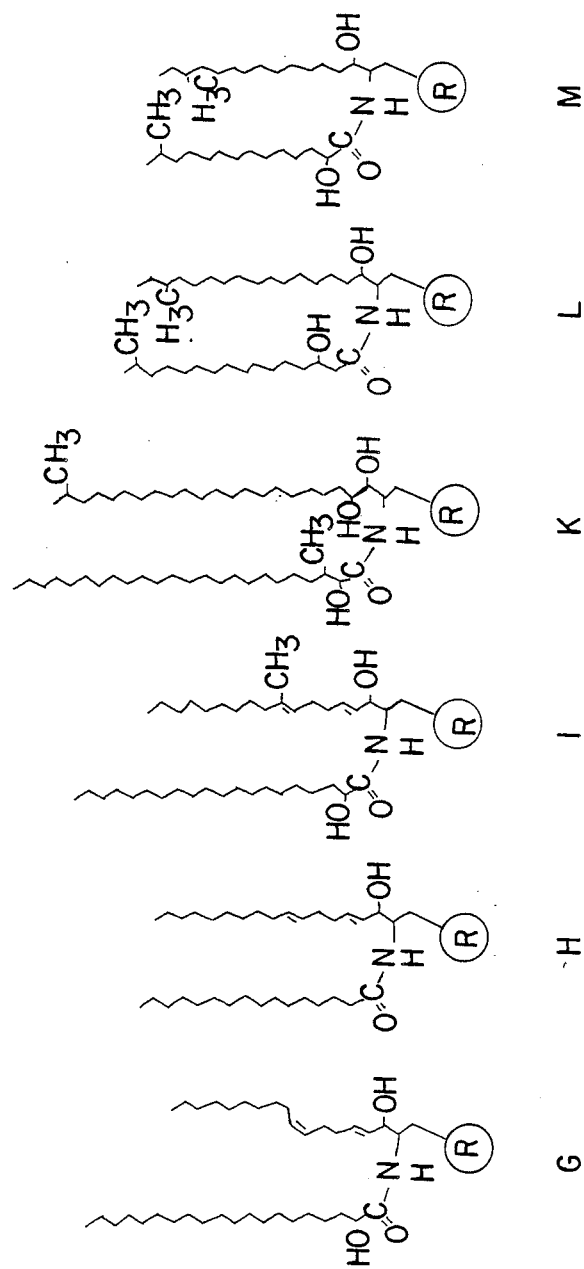

Chemical synthesis of the second-step receptor (GalβCer or GlcβCer) may be performed in various ways as referred to above and reviewed in detail in reference 13. For example, dihydrosphingosine (base of formula A in FIG. 5) may be prepared according to Carter et al. or Jenny and Grob (see reference 13). Hydroxy fatty acid may be coupled to this using the p-nitrophenylester (Pascher, *Chem. Phys. Lipids* 12, 1974, pp. 303-315) of 2-D-acetoxyoctadecanoic acid (Karlsson et al., *Chem. Phys. Lipids* 12, 1974, pp. 65-74). After the preparation of the 3-O-benzoyl derivative, the acetobromo derivatives of Gal or Glc may be used to prepare GalβCer or GlcβCer (substances 1 and 2, respectively, in Table 3).

Synthetic Receptor Analogues and Related Substances

Mono- or oligosaccharides coupled to a lipid part of multivalently to bovine serum albumin (substances 1-5 and 10-14 of Table 1) were purchased from The Sugar Company, Arlöv, Sweden. Novel receptor analogues of relevance for the present invention (substances 6-9 and 15-18 of Table 1) were prepared by and received from Dr. Göran Magnusson, Department of Organic Chemistry 2, University of Lund, Sweden (Dahmen et al., *Carbohydr. Res.* 118, 1983, pp. 292-301; Dahmen et al., ibid. 127, 1984, pp. 27-33). The receptor analogues employed are shown in Table 1 below.

TABLE 1

Synthetic receptor analogues used for inhibition or binding
(Sugars are of D configuration and in pyranose form)

| # | Structure |
|---|---|
| 1 | Gal of GalβCETE |
| 2 | Glc or GclβCETE |
| 3 | Galβ1 ⟶ 4Glc or Galβ1 ⟶ 4GlcβCETE |
| 4 | GalβCETE—BSA |
| 5 | GlcβCETE—BSA |
| 6 | Galβ1 ⟶ 4GlcβOEt |
| 7 | Galβ1 ⟶ 4Glcβ ⟶ OCH$_2$CH(CH$_2$SO$_2$(CH$_2$)$_{10}$COOH)(CH$_2$SO$_2$(CH$_2$)$_7$CH$_3$) |
| 8 | Galβ1 ⟶ 4Glcβ ⟶ OCH$_2$CH(CH$_2$SO$_2$(CH$_2$)$_{10}$COOH)(CH$_2$SO$_2$(CH$_2$)$_{10}$COOH) |
| 9 | Galβ1 ⟶ 4Glcβ ⟶ OCH$_2$CH(CH$_2$SO$_2$(CH$_2$)$_{10}$CONH—BSA)(CH$_2$SO$_2$(CH$_2$)$_7$CH$_3$) |
| 10 | Galβ1 ⟶ 4GlcβCETE—BSA |
| 11 | GalβOTE |
| 12 | GlcβOTE |
| 13 | Galβ1 ⟶ 4GlcβOTE |
| 14 | Galα1 ⟶ 4GalβOTE |
| 15 | Galβ1 ⟶ 4Glcβ ⟶ OCH$_2$CH(CH$_2$S—(CH$_2$)$_{15}$CH$_3$)(CH$_2$S—(CH$_2$)$_{15}$CH$_3$) |
| 16 | Glcβ ⟶ OCH$_2$CH$_2$SO$_2$—(CH$_2$)$_{17}$CH$_3$ |

TABLE 1-continued

Synthetic receptor analogues used for inhibition or binding
(Sugars are of D configuration and in pyranose form)

17
$$Glc\beta \longrightarrow OCH_2CH \begin{matrix} CH_2SO_2-(CH_2)_{15}CH_3 \\ CH_2SO_2-(CH_2)_{15}CH_3 \end{matrix}$$

18
$$Gal\beta 1 \longrightarrow 4Glc \longrightarrow OCH_2CH \begin{matrix} CH_2SO_2-(CH_2)_{15}CH_3 \\ CH_2SO_2-(CH_2)_{15}CH_3 \end{matrix}$$

CETE: ($OCH_2CH_2SCH_2CH_2CO_2CH_3$)
OTE: ($OCH_2CH_2S(CH_2)_{17}CH_3$)
BSA: Bovine serum albumin.

Preparation of Epithelial Cells

Epithelial cells from fresh tissues were prepared in two ways: by washing and by scraping. Washing was performed with EDTA-containing phosphate buffer in intestinal loops as described in reference 19. A loop was filled with buffer and incubated in a water bath at 37° C. with gentle moving/stirring for a few minutes, after which the intestinal content was decanted off. This was repeated 5-10 times and each fraction was centrifuged and cells examined by microscopy and marker enzyme (alkaline phosphatase, thymidine kinase) analyses. Fractions containing pure epithelial cells were pooled and used for the preparation of glycolipids as outlined above. In this way, epithelial cells from the small and large intestine of several human individuals and of rat strains were analyzed. Human small intestine was also gently scraped with a spoon to obtain epithelial cells somewhat contaminated with non-epithelial residue. In a similar way, human urinary tract (urether) epithelial cells were obtained as well as epithelial cells from dog and mouse intestines. The small intestine of several other animals was analyzed, including cat, cod-fish, guinea-pig, hamster, hen and rabbit (see reference 20). In addition to mass spectrometry etc. for information on ceramide components, the samples were run on a borate-impregnated silica gel plate where monoglycosylceramides separate both according to Gal and Glc and the major ceramide combinations of sphingosine, phytosphingosine, non-hydroxy and 2-hydroxy fatty acid (see reference 21).

VIRUS PREPARATIONS AND ANTIBODIES

In the receptor assays used, bound virus was detected by anti-virus antibody. Polyclonal and monoclonal antibodies were prepared according to standard methods (Rose et al., eds., Manual of Clinical Immunology, Americ. Soc. Microbiol., Washington, D.C., 1980). The viruses tested were known viruses which were grown and defined in professional virus laboratories using established techniques (Lennette, ed., Manual of Clinical Microbiology, Americ. Soc. Microbiol., Washington, D.C., 1980). The specific viruses are shown in Table 2.

TABLE 2

Viruses shown to bind to the second-step receptor

| | Family | Member | Bilayer membrane envelope |
|---|---|---|---|
| DNA viruses | Adenoviridae | Adenovirus 2 and 7 | No |
| | Herpetoviridae | B95-8 EB virus | Yes |
| RNA viruses | Orthomyxoviridae | Influenza virus | Yes |
| | Paramyxoviridae | Mumps virus | Yes |
| | viridae | Sendai virus, G variant | Yes |
| | | Sendai virus, S variant | Yes |
| | Rhabdoviridae | Rabies virus, ERA strain | Yes |
| | Reoviridae | Rotavirus K8 | No |
| | | Reovirus 1, 2 and 3 | No |

Adenovirus 2 and 7 were propagated in A-549 cells and hyperimmune sera were obtained by established immunization of rabbits (Wadell, Curr. Top. Microbiol. Immunol. 110, 1984, pp. 191-220). Human rotavirus K8 was propagated in GMK cells and a rabbit hyperimmune serum was used (Urasawa et al., Microbiol. Immunol. 25, 1981, pp. 1025-1035). Reovirus 1, 2 and 3 were propagated in GMK cells and rabbit hyperimmune sera were used (Rose et al., eds., op. cit.; Lennette, ed., op. cit.). Epstein-Barr virus was the B95-8 EB virus and was propagated in lymphoid monkey cells and was prepared by Dr. L. Rymo (Rymo et al., Nucl. Acid Res. 5, 1978, pp. 1387-1402), and the antibody was mouse monoclonal antibody MA provided by Dr. G. Pearson, Dep. Microbiology, The Mayo Foundation, Rochester, U.S.A. The ERA strain of rabies virus was propagated in BHK-21 cells, the antibody was mouse monoclonal antibody 101-1 (Dietzschold et al., Proc. Nat. Acad. U.S.A. 80, 1983, pp. 70-74), and the preparations were provided by Dr. H. Koprowski (cf. Dietzschold et al., op. cit.). The influenza virus A/PR/8/34 was propagated in embryonated hen's eggs, the antibody was mouse monoclonal antibody H2-6A5, and these preparations were provided by Dr. W. Gerhard (Caton et al., Cell 31, 1982, pp. 417-427). Influenza virus strains X-31 and X-31 HS were propagated in embryonated hen's eggs and were provided by Dr. J. C. Paulson (cf. Rogers et al., Nature 304, 1983, pp. 76-78). These strains were detected by overlayering the thin-layer plate with a 2% suspension of human erythrocytes (red colour for active bands) for 1 hour and washing. Influenza virus strains A/Chile/1/83, A/Philippines/2/82 and B/USSR/100/83 were obtained from SBL (Swedish State Bacteriological Laboratory), Solna, Sweden. These viruses were also detected by overlayering with human erythrocytes. The Z strain of Sendai virus ("S" and "G" variants; see reference 46 and Example 1) was grown in embryonated hen's eggs or in Vero cells, and the antibody was mouse monoclonal antibodies 817 and 851 (Örvell et al., J. Immunol. 129, 1982, pp. 2779-2787)

and rabbit anti-Sendai antibody 121 prepared by Dr. C. Örvell. The Kilham strain of mumps virus was propagated in Vero cells and the antibody was mouse monoclonal antibody (Örvell, J. Immunol. 132, 1984, pp. 2622-2629). HTLV-I virus was prepared by Dr. J. Blomberg from an HTLV-I secreting leukemic T cell line (cf. Blomberg et al., Leukemia Res., 1985, in press). HTLV-III was provided by Dr. R. C. Gallo, National Cancer Institute, NIH, Bethesda, U.S.A. HTLV-I and HTLV-III viruses were iodinated using the standard lactoperoxidase technique (Rose et al., Manual of Clinical Immunology, Americ. Soc. Microbiol., Washington, D.C., 1980).

The antibodies were tested for the absence of unspecific binding in the binding assay system using all ingredients except virus. In this way, it was excluded that the antibodies bound directly to specific glycolipid bands, which phenomenon otherwise may produce falsely positive results.

Assays for Virus Binding Specificity and Estimation of Relative Binding Strength The assay for the detection of virus binding to glycolipids and for testing of detailed specificity of binding has been developed by the present inventors and is of decisive importance for the invention (cf. Hansson et al., FEBS Lett. 170, 1984, pp. 15-18). In principle, the virus to be assayed is layered on a chromatogram with separated glycolipids from target cells or other sources and allowed to interact with potential receptor substances. After careful washings, bound virus is detected by anti-virus antibody and radiolabelled anti-anti-body followed by autoradiography. In some cases, the virus particle was directly labelled before binding. The detailed procedure is as follows:

Mixtures of total lipids (up to 100 $\mu$g in each lane) or total glycolipids (20-40 $\mu$g in each lane) or pure glycolipids (0.01-1 $\mu$g) were separated on aluminum sheets, about 5×5 cm, coated with silica gel 60 (Merck), usually with chloroform/methanol/water (60:35:8, by volume) as the solvent for non-acid glycolipids, and with chloroform/methanol/2.5M ammonia (60:40:9, by volume) as the solvent for acid glycolipids. For purposes of comparison, a parallel plate is detected chemically by spraying and heating with anisaldehyde solution. For virus binding, the dried chromatogram with separated substances is dipped for 1 minute in 200 ml of diethylether containing 0.5% (w/v) of polyisobutylmethacrylate (Plexigum P28, Röhm GmbH, Darmstadt) and dried for 2 minutes. The plate is then sprayed with phosphate-buffered saline (PBS) of pH 7.3 containing 2% bovine serum albumin (BSA) and 0.1% NaN$_3$ (solution A) and then immersed in solution A and placed in a Petri dish for 2 hours. After tipping off solution A, the virus suspension is added (about 25 $\mu$g per ml with about 2 ml for a plate of the dimensions given above) to the chromatogram placed horizontally in the humidified atmosphere of a Petri dish. After incubation for 2 hours, the virus suspension is tipped off and the plate is washed six times with PBS, 1 minute each time. In a typical case of antibody, monoclonal antibody 817 directed against Sendai virus produced in ascitic fluid is diluted 1:100 with solution A, using about 2 ml per plate, with incubation for 2 hours. After washing five times with PBS, about 2 ml of rabbit anti-mouse Fab is incubated for 2 hours (4×10$^5$ cpm/ml of $^{125}$I-labelled F(ab')$_2$, the Radiochemical Centre, Amersham). After six washings in PBS, the plate is dried and exposed to XAR-5 X-ray film (Eastman), usually for 2-3 days, using an intensifying screen.

The treatment with plastic produces a hydrophobic surface. Separated glycolipid or other bands are thus induced to be exposed on the hydrophobic solid surface similar to the way lipids are exposed in the biological membrane. This means that the test substance is densely anchored with its paraffin chains in the plastic surface with the polar head groups exposed and accessible to the environment. This mimics the surface monolayer of the living cell. This plastic treatment is highly critical for specificity and reproducibility and explains the advantage of this solid-phase method over traditional inhibition based on "solubilized" aggregates or micelles (see reference 22).

The detection limit varies with the avidity of the ligand but is in the range of 5-50 ng of receptor, or in about the same picomole range. For a receptor candidate to be considered negative in the tabulated results, there should be no darkening at a one or more microgram level. Good binders give saturating black bands at 100 ng. An obvious advantage of this assay is that mixtures of substances are first separated into substance species, avoiding the risk of shielding of minor components, or false negative binding due to contaminating substances. Also, the coating with albumin blocks unspecific hydrophobic sites, which otherwise may cause false positive results. Finally, the extensive washings remove more loose unspecific associations. By comparison, traditional inhibition assays usually incubate virus with target cells in suspension in the absence or presence of sonicated micelles. In case of the hemolysis assay, simple photometry is done on the mixture after centrifugation (cf. Huang. Lipids 18, 1983, pp. 489-492). Thus, no albumin is present, and there are no washing steps analogous to the present assay.

For quantification of virus binding, a technique was adopted from the analogous solid-phase binding or antibodies to microtiter wells (Brockhaus et al., J. Biol. Chem. 256, 1981, pp. 13223-13225). A dilution series of glycolipid or other substances in 50 $\mu$l of methanol is allowed to evaporate in the microtiter well overnight at room temperature. 100 $\mu$l of 2% BSA in PBS are then incubated for 2 hours after which the well is rinsed once with this volume and solution. 50 $\mu$l of a suspension of 1.5 $\mu$g of virus in BSA-PBS is incubated for 4 hours, followed by four washings with 100 $\mu$l each of BSA-PBS. In case of Sendai virus, 50 $\mu$l of ascitic fluid-produced antibody 817 diluted 1:100 in solution A is incubated for 4 hours followed by four washings. Finally, 50 $\mu$l of rabbit anti-mouse Fab (2.5×10$^4$ cpm $^{125}$I-labelled F(ab')$_2$, the Radiochemical Centre, Amersham) is incubated overnight at 4° C. followed by five 100 $\mu$l washings with BSA-PBS. The wells are cut from the plate and assayed individually for $^{125}$I in a spectrometer.

Inhibition Studies

Attempts to inhibit the binding of virus by means of the two assays described above were done by a preincubation of the virus for one or two hours with up to 2 mg per ml of free saccharide or BSA-conjugated saccharide in PBS or BSA-PBS. This mixture is then added in toto to the plate or well.

Inhibition studies were also performed by means of an ELISA technique (enzyme-linked immunosorbent assay) as follows (see reference 1 and Rose et al., eds., Manual of Clinical Immunology, Americ. Soc. Microbiol., Washington D.C., 1980). In this case, microtiter wells (type Cooks M 29) were coated with glycolipid in methanol as described above, or with rabbit anti-Sendai antiserum as a standardized control (see reference 1). The glycolipids used were GalβCer, which is a virus binder, see glycolipid 1 to Table 3 (about half of the fraction contained non-hydroxy fatty acid and this species is inactive), and globoside, which is a non-binder, see glycolipid 16 of Table 3, both at 500 ng per well. 50 μg/ml of antiserum in sodium bicarbonate buffer, pH 9.6 (100 μl/well) were added. The wells were then saturated for 2 hours at 37° C. with 2% BSA in 50 mM Tris-HCl and 0.15 M NaCl buffer, pH 8.5, and then washed twice with this buffer containing 1% BSA. 1.5 μg per well of Sendai virus in 100 μl of the 1% BSA buffer were incubated for 2 hours, followed by four washings with 100 μl each of the 1% BSA buffer. Detection of bound virus was carried out by incubation for 1.5 hours at 37° C. with 100 μl of antibody 851 diluted 1:100 with buffer, followed by four washings with 100 μl each of the buffer. 100 μl of horseradish peroxidase-conjugated rabbit anti-mouse antibody (Dakopatts, Glostrup, Denmark; P 161, 10 mg/ml diluted 1:500) were incubated for 1.5 hours at 37° C. followed by four washings with buffer. 100 μl per well of OPD solution (4 mg of orthophenylenediamine, Sigma, dissolved in 10 ml of 0.1M sodium citratephosphate buffer, pH 5.0 to which had been added 4 μl of 30% $H_2O_2$) were incubated for 15 minutes, and then the reaction was stopped by adding 50 μl of 0.5M $H_2SO_4$ per well. Optical reading was performed at 492 nm. Typical values were as follows: all steps except virus=0.150; binding to globoside=0.200; binding to GalβCer=0.650; binding to antiserum=1.7.

Inhibition of virus binding by substance 9 of Table 1 was performed as follows. About 2 μg of virus were preincubated in a siliconized test tube with about 200 μg of substance 9 for 2 hours at 37° C. and then transferred in 50 μl portions to the wells and incubated for 1 hour at 37° C., followed by four washings with the buffer containing 1% BSA. The subsequent steps were carried out as described above. Substance 9 was diluted 1:4 in 7 separate preincubation steps.

Preliminary experiments were also performed on the inhibition of virus binding in the two assays described by preincubating the virus as above with sonicated micelles of amphipathic glycolipids and other substances. This was done for Sendai virus. Plaque inhibition test (Lycke et al., eds., *Textbook of Medical Virology*, Butterworths, London, 1983) was done with the ERA-similar virus strain CVS-3337 as follows:

Phosphatidylcholine (200 μg), cholesterol (100 μg) and Galβ1→4GlcβCer with 2-hydroxy fatty acid (230 μg) or the first two lipids and phosphatidylserine (200 μg) were dissolved in chloroform/methanol and the solvent evaporated in a tube. 4 ml of PBS were added and the mixture sonicated in a Vetrasonics model W-370 for ½ hour at room temperature. The virus was diluted with PBS to give approximately $4 \times 10^3$ plaque-forming units per ml. 0.5 ml virus and 0.5 ml sonicated micelles (or PBS as control) were incubated for 3 hours at room temperature. Dilutions and titration of remaining infectious virus on CER cell monolayers are carried out under standard conditions (Lennette, ed., *Manual of Clinical Microbiology*, Americ. Soc. Microbiol., Washington D.C., 1980).

EXAMPLE 1

Discovery of the Second-Step Receptor

Figure 2:
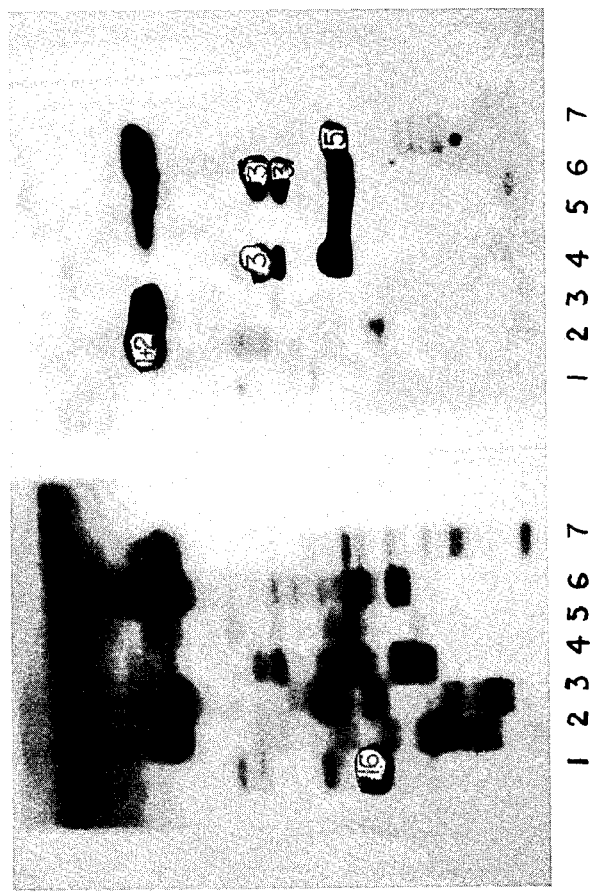
FIG. 2 shows an assay of Sendai virus (S variant) binding to the second-step receptor, analyzed as described in Materials and Methods. This illustrates the possible analysis of a large number of receptor candidates as mixtures of glycolipids of various origins (screening for receptors) possible with this assay. To the left is the chromatogram after chemical detection with anisaldehyde and to the right the autoradiogram after an overlay of virus over the same lanes. The following are the total non-acid glycolipids shown: human erythrocytes (lane 1), human meconium (lane 2), intestine from *Macaca cynomolgus* (lane 3), dog small intestine (lane 4), rabbit small intestine (lane 5), guinea-pig small intestine (lane 6), and mouse large intestine (lane 7). The white numbers refer to substances listed in Table 3. It appears that a large number of major glycolipid bands detected chemically (left) do not bind the virus (right), indicating the high selectivity and specificity of the assay.

Sendai virus was used as the model virus for analysis (cf. the overlay assay method described in Materials and Methods) because it is relatively well studied with respect to its binding to neuraminic acid-containing receptors (the first-step receptor) (see reference 26) (FIGS. 1 and 2 illustrate the binding of the virus to the conceptual first-step and second-step receptors, respectively). Preparations of the virus prepared as described in Materials and Methods were analyzed, and two previously unknown receptor binding variants of the Z strain were shown to carry separate specificities in the case of binding to neuraminic acid-containing glycolipids (gangliosides). The S variant bound to gangliosides of human erythrocytes only but not to gangliosides of the human brain (FIG. 1). The G variant, on the other hand, bound to gangliosides of both sources (not shown). It is known that the gangliosides of the two sources are structurally related but differ in their core sequences. Thus, cleavage of neuraminic acid by the enzyme neuraminidase from the gangliosides completely abolishes binding of the two virus preparations. This shows that the binding to gangliosides is completely dependent on the presence of neuraminic acid but that the binding epitope of the glycolipids also includes the non-neuraminic acid parts, which differ between brain and erythrocyte. Therefore, the first-step receptor specificity in these two cases differ and should correspond to separate, chemically different sites on the two viruses recognizing the receptors. That several bands in the assay may bind is explained by the presence of the receptor epitope on core substances of various sizes which differ in chromatographic mobility. The fact that the G variant of the virus binds to gangliosides of both origins may be explained by a less strict specificity in the binding compared to the S variant.

In contrast to the different binding to gangliosides (first-step receptors), the two variants bind the second-step receptors in an identical way. This is shown for the S variant in FIG. 2. As will be explained in further detail in Example 2, this binding is to glycolipids lacking neuraminic acid and is thus chemically distinct from the first-step binding.

This shows that a virus may have two chemically distinct and separate receptors. Furthermore, the results obtained from the assay illustrate the specificity of the method as explained in the specification and in Materials and Methods. The selective binding is evident when comparing the patterns obtained by autoradiography (virus binding) with chemical spraying (all substances visualized). Some major bands appearing from spraying and being structurally closely related to receptor substances are completely negative for virus binding (cf. Example 2).

EXAMPLE 2

Analysis of Natural Receptor Candidates for Binding Specificity with Respect to Several Viruses A large number of receptor candidates (Table 3) was analyzed for binding activity using the overlay assay described in Materials and Methods.

TABLE 3

| No. | Glycolipid structure | Virus binding |
|---|---|---|
| 1 | GalβCer | + |
| 2 | GlcβCer | + |
| 3 | Galβ1→4GlcβCer | + |
| 4 | Galα1→4GalβCer | + |
| 5 | Galα1→3Galβ1→4GlcβCer | + |
| 6 | Galα1→4Galβ1→4GlcβCer | + |
| 7 | Fucα1→2Galβ1→4GlcβCer | + |
| 8 | GlcNAcβ1→3Galβ1→4GlcβCer | + |
| 9 | GalNAcβ1→4Galβ1→4GlcβCer | + |
| 10 | NeuAcα2→3Galβ1→4GlcβCer | − |
| 11 | Galα1→3(Fucα1→2)Galβ1→4GlcβCer | + |
| 12 | GalNAcα1→3(fucα1→2)Galβ1→4GlcβCer | − |
| 13 | Galα1→3Galα1→4Galβ1→4GlcβCer | − |
| 14 | Galβ1→3GlcNAcβ1→3Galβ1→4GlcβCer | + |
| 15 | Galβ1→4GlcNAcβ1→3Galβ1→4GlcβCer | + |
| 16 | GalNAcβ1→3Galα1→4Galβ1→4GlcβCer | − |
| 17 | Galβ1→3GalNAcβ1→4Galβ1→4GlcβCer | − |
| 18 | Fucα1→2Galα1→3Galα1→4Galβ1→4GlcβCer | − |
| 19 | Fucα1→2Galβ1→3GlcNAcβ1→3Galβ1→4GlcβCer | − |
| 20 | Fucα1→2Galβ1→4GlcNAcβ1→3Galβ1→4GlcβCer | − |
| 21 | Galβ1→3(Fucα1→4)GlcNAcβ1→3Galβ1→4GlcβCer | + |
| 22 | Galβ1→4(Fucα1→3)GlcNAcβ1→3Galβ1→4GlcβCer | + |
| 23 | NeuAcα2→3Galβ1→4GlcNAcβ1→3Galβ1→4GlcβCer | − |
| 24 | Fucα1→2Galβ1→3(Fucα1→4)GlcNAcβ1→3Galβ1→4GlcβCer | − |
| 25 | Fucα1→2Galβ1→4(Fucα1→3)GlcNAcβ1→3Galβ1→4GlcβCer | − |
| 26 | Galβdiglyceride | + |
| 27 | Galα1→6Galβdiglyceride | + |

1-25: Animal origin, 26-27 plant origin. The monosaccharides are of D configuration except Fuc which is L, and are all in pyranose form.
+ indicates binding and − indicates lack of binding.

Mixtures of extracts from target cells or tissues for viral infections extracted by means of organic solvents as described in Materials and Methods were pre-separated on the chromatogram surface allowing the detection of active substances after overlaying with the virus preparation in question. A binding substance was isolated and structurally characterized and used in pure form for more detailed binding studies. Sendai virus was first used in these analyses. As one single overlay assay may contain more than 100 substances of a diverse structure, a very efficient selection of actual receptors was obtained. Using human and animal tissues of various kinds like nerve tissue, blood, gastrointestinal tract, urinary tract, and including both adult and fetal tissues, only the glycolipids marked with a + in Table 3 and further defined in Table 4 were shown to be receptors. There was no binding at relevant levels of other surface membrane or other substances like cholesterol or various glycerophospholipids that were coextracted in the procedures employed. On the other hand, several of the viruses analysed (cf. Table 2), including Sendai virus (cf. Example 1), showed a glycolipid binding different from that of Tables 3 and 4 which was chemically distinct and corresponded to the first-step receptor.

Figure 3:
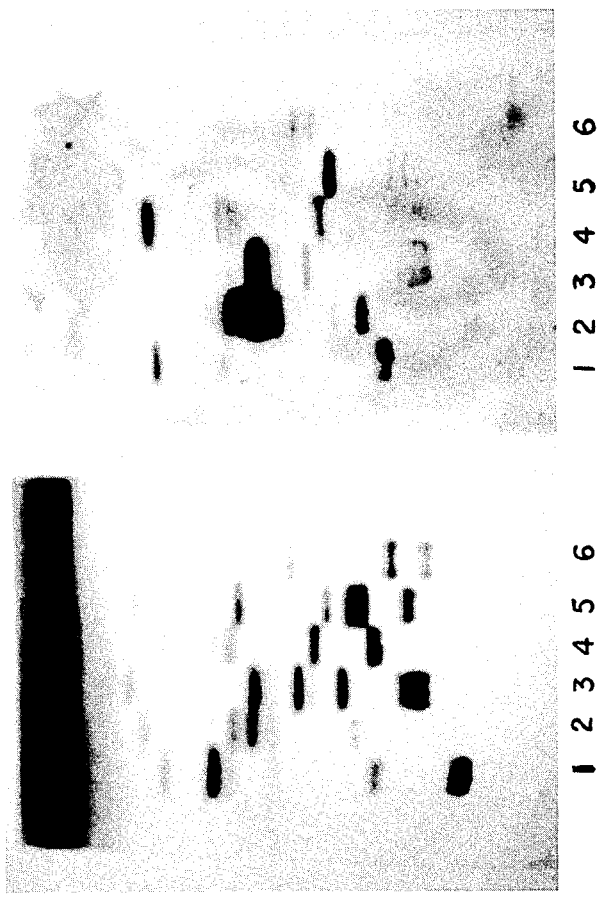
FIG. 3 shows an assay of Sendai virus (S variant) binding to the second-step receptor substances, analyzed as described in Materials and Methods. This illustrates the binding to substances which are synthetic or have been isolated from natural sources and identified chemically. To save space, several pure substances were added to the same lane, starting with the most rapid-moving substance as shown in the chromatogram to the left, detected by anisaldehyde. The autoradiogram is shown to the right. The figures refer to Table 3. Lane 1: synthetic 2 with phytosphingosine and 2D-hydroxystearic acid, 3 with non-hydroxy fatty acid, 15, and GalNAcα1→3(Fucα1→2)Galβ1→4-(Fucα1→3)GlcNAcβ1→3Galβ1→4GlcβCer; lane 2: synthetic 2 with phytosphingosine and stearic acid, 3 (three closely moving bands with 2-hydroxy fatty acid), and 15 with non-hydroxy fatty acid; lane 3: synthetic 2 with sphingosine and stearic acid, 3, 6 with non-hydroxy fatty acid (contaminated), 16, and 22 (three closely moving bands with 2-hydroxy fatty acid); lane 4: synthetic 1 with phytosphingosine and 2-hydroxy stearic acid, 3 with phytosphingosine and non-hydroxy fatty acid, 6, and GalNAcα1→3GalNAcβ1→3Galα1→4Galβ1→4GlcβCer with non-hydroxy fatty acid; lane 5: synthetic 1 with sphingosine and stearic acid, substance 13 of Table 1, 6 (short-chain 2-hydroxy fatty acid), 16 (two closely moving bands with 2-hydroxy fatty acid), and 17 (three closely moving bands in the autoradiogram to the right may be contaminants in 17); lane 6: 8 (two closely moving bands), 20, and GalNAcα1→3(Fucα1→2)Galβ1→4GlcNAcβ1→3Galβ1→4GlcβCer.

An important finding was that the binding to the natural receptors depends on the composition of the lipophilic part of the glycolipid, the ceramide, as defined in Table 4 and illustrated for some species in FIG. 3. Only species with 2-D-hydroxy fatty acid in the ceramide are active. Therefore, all natural glycolipids used for detailed testing concerning the importance of variation in the carbohydrate part (Table 3) were chosen for the presence of 2-hydroxy fatty acid. Species referred to in Table 3 as being positive are active when containing 2-hydroxy fatty acid but inactive when containing non-hydroxy fatty acid.

The virus is able to bind glycolipids with up to five sugars (Table 3). However, quantitative binding studies (cf. Materials and Methods) reveal that the one-sugar substances GalβCer and GlcβCer are the best binders.

Figure 4:
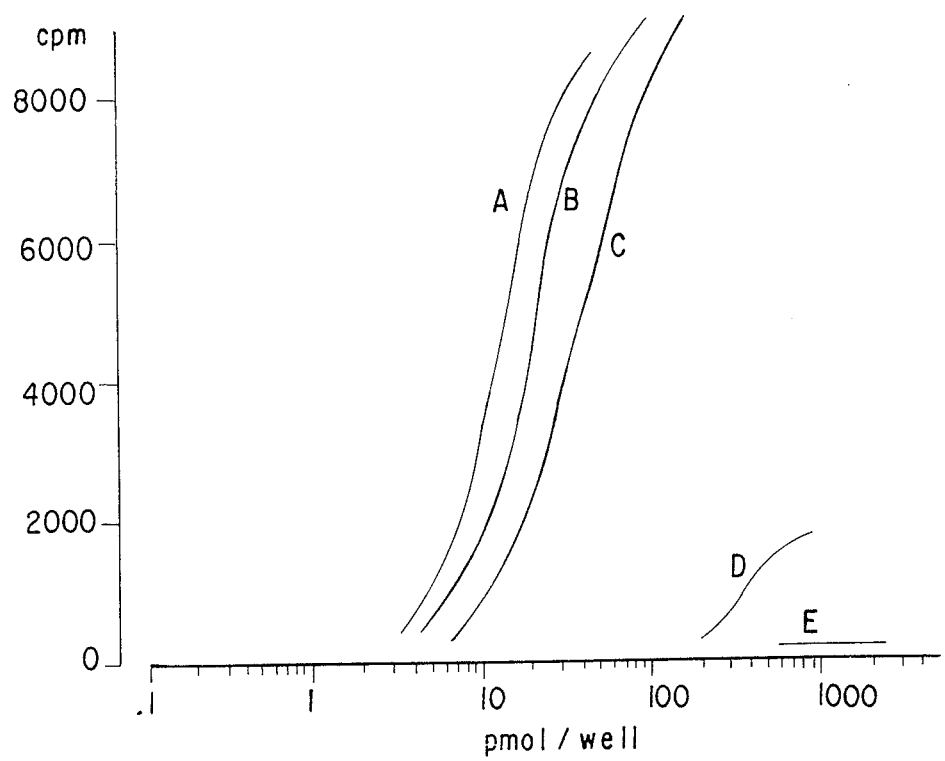
FIG. 4 shows the curves obtained from the quantitative binding (cf. Materials and Methods) of Sendai virus to various synthetic or natural glycolipids, obtained as described in Materials and Methods. Dilutions of glycolipids were adsorbed in microtiter wells (x axis) and virus binding was, after incubation, estimated as radioactivity (y axis). The letters refer to the following samples tested: A is substance 1 or 2 in Table 3. B is the first-step receptor with the following sequence: NeuAcα2→3Galβ1→4GlcNAcβ1→3(NeuAcα2→3Galβ1→4GlcNAcβ1→6)Galβ1→4Glc-NAcβ1→3Galβ1→4GlcβCer. C is substance 3 in Table 3 (with 2-hydroxy fatty acid) or substance 18 in Table 1. D is substance 5 in Table 3. E may be substances 21 and 22 in Table 3 (which bind weakly in the chromatogram, see FIG. 3, lane 3 for substance 22) or the substances which are negative in Table 3.

In FIG. 4, curve A represents these two glycolipids. Curve C represents the two-sugar glycolipid 3 of Table 3 and curve D represent the three-sugar glycolipid 5. It is important to note that the avidity (strength) of binding for this second-step receptor is on the same order of magnitude as that of the established first-step receptor (curve B). The binding to larger glycolipids is therefore explained by a recognition of an internal part of the molecules. Such an unconventional binding is not unexpected in view of the inventors' results from carbohydrate receptor binding for several bacteria and bacterial toxins (see reference 23, 25 and 46). The fact that some (the major part) of the glycolipids tested do not bind although they contain the binding epitope, e.g. →4GlcβCer, is rationalized by a steric hindrance in the access of the large virus particle to this one-sugar epitope. It is also further evidence for a stereospecificity at the molecular level, allowing the use of the concept of receptor specificity, and strongly arguing against an unspecific interaction.

Of interest to wider applications, plants are known to contain receptor glycosphingolipids (see reference 41). Substance 2 of Table 3 with 2-hydroxy fatty acid is a dominating glycolipid in plant leaves. Also, substances 26 and 27 shown to bind Sendai virus are relatively abundant in plants and may serve as receptors for plant viruses.

The finding that there is no binding to free ceramide (lacking carbohydrate) is important for the interpretation of the binding epitope of the receptor substances. Furthermore, in the assay, there is no inhibition of binding of virus to receptors when adding various free oligosaccharides or oligosaccharides, e.g. Galβ, Glcβ or Galβ1→4Glcβ, coupled multivalently to albumin (cf. Example 6). From this it may be concluded that there is binding to the glycolipid only; neither ceramide alone nor saccharide alone (or coupled to a protein) is able to interact with the virus.

The curves obtained from the quantitative binding studies (FIG. 4) indicate that the avidity of the binding is very similar for the first-step and second-step receptors (curve B and A, respectively). As the first-step receptor has already been studied for biological relevance (see reference 3), this means that the binding avidity for the second-step receptor is at a biologically adequate level. Also, the best second-step binder is that with one sugar (compare curves A, C and D), and some binders with several sugars do not raise up (curve E) although the binding is clearly detectable in the overlay assay (Table 3).

Figure 6:
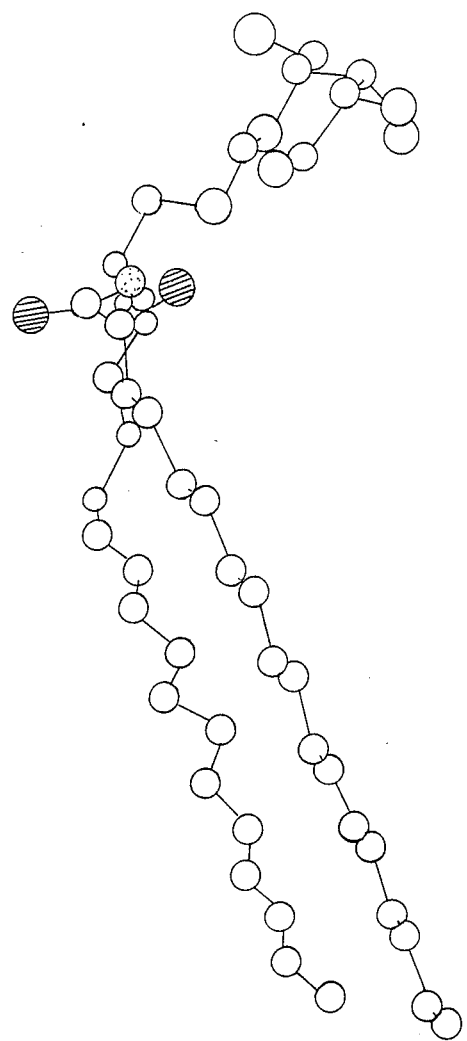
FIG. 6 shows the conformation of the second-step receptor as obtained by single crystal X-ray crystallography of synthetic substance 1 of Table 3 with dihydrosphingosine and 2D-hydroxy stearic acid (cf. Pascher et al., *Chem. Phys. Lipids* 20, 1977, pp. 175-191). The nitrogen is dotted and the carbonyl oxygen and C20 of the acid are hatched. The substance was synthesized as described in Pascher, *Chem. Phys. Lipids* 12, 1974, pp. 303-315, and crystallized from 95% of ethanol. The X-ray data were collected on a Picker FACF I defractometer and more than 5000 independent reflections were measured. All calculations were performed on a DEC-10 computer system using mainly the X-RAY 72 programme system.

A second conclusion from quantitative analyses by means of this assay is that the binding is of the low-affinity type needing multivalency to be efficient. This is based on a comparison, in the same assay, of virus binding with the binding of several bacteria and bacterial toxins to their respective receptor glycolipids. Several bacteria (see reference 23 and 46) and the Shiga toxin (see reference 25 and 46) bind similarly to the virus (the curves raise at similar levels of receptor dilution). On the other hand, in case of cholera toxin (similar size as Shiga toxin), the raise of the curve is shifted to the left at a $10^2$–$10^3$ greater receptor dilution. These different locations of the curves coincide with the possibility to inhibit ligand binding to the receptor glycolipids using soluble, univalent oligosaccharide receptor analogues. Cholera toxin is easily inhibited but for Shiga toxin, there is no detectable inhibition at the level of 5 mg/ml of the receptor disaccharide. However, the Shiga toxin is easily inhibited using the disaccharide coupled multivalently to albumin. The conclusion is a high-affinity binding in case of cholera toxin and a low-affinity binding in case of the Shiga toxin, the latter needing multivalency to be efficient. A similar situation as for Shiga toxi exists for several bacteria. As the curves for virus binding coincide with those of Shiga toxin and several bacteria but not with that of cholera toxin, the virus binding is of the low-affinity type. Therefore, application of the natural binding epitope for virus binding would seem to need a multivalent presentation. This is present in the binding assays and in the biological membrane (Example 4) and corresponds to a multiplicity of binding proteins on the virus surface.

The approach described above for Sendai virus was extended to a series of other viruses, representing most of the known virus families (Table 2). All viruses shown in Table 2 were shown to bind in a way which was very similar to Sendai virus in the case of the second-step receptor, although several of them also showed a separate first-step receptor analogous to that of Sendai virus (Example 1). The analyses of these viruses was performed using the virus preparations and antibodies for detection as described in Materials and Methods. To cover as many receptor candidates as possible, the glycolipid mixtures employed for the assay shown in FIG. 2 were used. Additionally, several isolated substances of Table 3 were used in dilutions on the thin-layer plate to test the avidity of binding compared to Sendai virus. The results showed that all viruses tested had a binding pattern identical with or very similar to that of FIG. 2, with similar binding avidity. This means that the viruses tested have a specific binding property in common which should correspond to a common binding protein on the virus surface. This property does not depend on the different envelopes of the viruses or the character of the genome (Table 2). Therefore, morphologically and genetically different viruses causing a wide variety of human and animal diseases affecting separate organ systems possess a common binding property, namely a second-step receptor which is probably used for penetration.

EXAMPLE 3

Chemical Characterization of Receptors and Analysis of the Ideal Conformation of the Binding Epitope As described in Materials and Methods, individual receptor-active substances were isolated in pure form and chemically characterized. This gave information both on the structure of the polar/hydrophobic part (i.e. the saccharide structure including type of sugars, sequence, position of binding, anomerity and ring size) and the non-polar part (i.e. the ceramide, including fatty acid chain structure as regards their length, branching and degree of unsaturation and the position and configuration of the hydroxyl groups, and the long-chain base structure as regards the length of the paraffin chain, unsaturation, and the position and configuration of functional groups). The methods used were high technology mass spectrometry (see reference 14) and NMR spectroscopy (see reference 15) in addition to conventional degradation methods. To get a wide range of structures for testing, tissues from different animals were used as preparative sources (see reference 13a and 33). Some of the epithelial tissues used have been described concerning glycolipid structures such as human intestine (see reference 42 and 43), rat intestine (see reference 13a), mouse intestine (see reference 20 and 44), dog intestine (see reference 45), and intestines from cat, cod-fish, guinea-pig, hamster and rabbit (see reference 20). Several other tissues were alos analyzed as described in Example 2. Many of these structures have recently been reviewed (see reference 13). This means that a very large number of glycolipids and other substances not included in Table 3 were analyzed but found negative for binding to Sendai virus.

A very important feature is the dependence of binding on the ceramide structure, as summarized in Table 4 for one particular glycolipid, No. 3 of Table 3, isolated from the indicated natural sources and carefully analyzed for its detailed structure. The experiments were performed as described in Materials and Methods using the overlay binding assay. Criteria for positive binding were also defined. The glycolipids tested were defined by the structural methods described in Materials and Methods. The detailed structures of various molecular species of ceramides are shown in FIG. 5. The letters in Table 4 also refer to this Figure.

TABLE 4

Effect on virus binding of the ceramide structure of the glycolipid

| Combination of fatty acid and long-chain base | Source of preparation | Virus binding |
|---|---|---|
| B: Non-hydroxy fatty acid-sphingosine | Human erythrocytes | − |
| C: Non-hydroxy fatty acid-phytosphingosine | Dog small intestine | (+) |
| D: 2-Hydroxy fatty acid-sphingosine | Dog small intestine | ++ |
| E: 2-Hydroxy fatty acid-phytosphingosine | Rat small intestine | ++ |

−: no binding
(+): weak binding
++: good binding

Thus, although the oligosaccharide structure is identical for the four variants, only those having a 2-D-hydroxy fatty acid in the ceramide bind the virus. This was repeatedly reproduced for other glycolipids of Table 3 as well. This, at first sight, appears to mean that the 2-hydroxy group is specifically involved in the binding. However, binding studies of various synthetic glycolipids rule this out (Example 5). Instead, the interpretation is that glycosphingolipids with a 2-hydroxy fatty acid differ in conformation from glycosphingolipids having a non-hydroxy fatty acid. This has been documented by X-ray crystallographic analysis of the former (see reference 31) and NMR analysis of the latter (see reference 32). In these cases, synthetic one-sugar glycosphingolipids were used. The 2-hydroxy glycosphingolipid has a spoon-like or shovel-like conformation (cf. FIG. 6) with the saccharide ring positioned at an angle of about 110° in relation to the ceramide. In the non-hydroxy isomer, this angle is about 180°. Going through all other structural parameters of the substances analyzed, this is the only common denominator of interpretation. Therefore, as discussed above, the importance of the 2-hydroxy group of the glycosphingolipid is to present the first saccharide in the proper bent preferred conformation. This makes the $\alpha$ side of this sugar accessible for binding, which has therefore been interpreted as part of the binding epitope. In the presentation of the sugar (more or less at right angles to the membrane-like surface of the assay) in the case of the non-hydroxy glycosphingolipids, this binding epitope is not likely to be accessible for virus binding.

EXAMPLE 4

Figure 7:
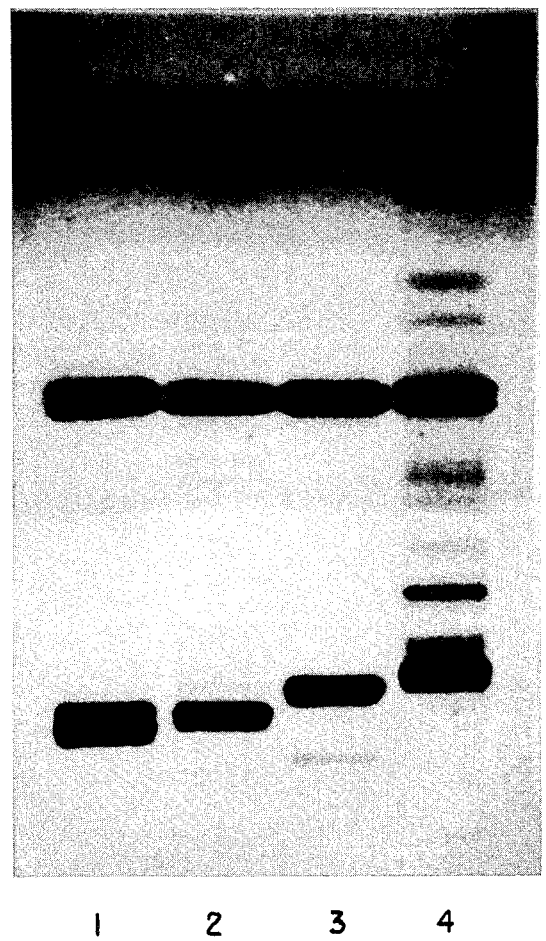
FIG. 7 shows a thin-layer chromatogram detected with anisaldehyde to illustrate the existence of second-step receptor glycolipids in epithelial cells of the human small intestine. Epithelial cells and total non-acid glycolipids were prepared and identified as described in Materials and Methods. The double bands which are common to the four lanes have been identified as a mixture of 1 and 2 of Table 3, the two most optimal natural virus binders (Example 2 and FIG. 4). The more slow-moving glycolipids are blood group fucolipids and vary among the four individuals analyzed which were of the following blood group phenotypes. Lane 1: A₁Le (a−b+), secretor; lane 2: OLe (a−b+), secretor; lane 3: OLe (a+b−), non-secretor, lane 4: OLe (a−b−), secretor. The composition of these samples has been described by Björk et al., in Cartron et al., eds., *Red Cel Membrane Glycoconjugates and Related Genetic Markers*, Libraire Arnette, Paris, 1983, pp. 125-137.

Receptors on Target Cells at the Port-of-Entry of Viral Infections, and on Certain Other Cells As described in Examples 2 and 3, a large number of epithelial tissues of different animals have been used by the present inventors as sources for the preparation of glycolipids. To test more precisely the location of receptor glycolipids to the epithelial cells which are the direct targets of viral infections, such cells were isolated as described in Materials and Methods. The technique was worked out for rat intestinal cells (see reference 19) including both small and large intestine, and was applied also on human small and large intestine. Also, a mucosa scraping was performed on human intestine (see reference 42) and human urether. A common denominator of all epithelial samples analyzed (cf. Materials and Methods), regardless of tissue or animal source, is the existence of Glc$\beta$Cer (substance 2 of Table 3 with 2-hydroxy fatty acid) and in many cases also Gal$\beta$Cer with 2-hydroxy fatty acid. Therefore, the most optimal natural Sendai virus binders (curve A of FIG. 4) exist generally in epithelial cells. As an illustration, FIG. 7 shows the result from an analysis of epithelial cells of small intestine of four human individuals of different blood group phenotypes. While, as expected, the slow-moving blood group fucolipids vary between the samples, they have the receptor-type glycolipids in common. Therefore, all cells which the virus invades when infecting an organism contain the second-step receptor.

Non-epithelial cells have much lower amounts or may practically lack these receptor glycolipid species. Contrary to what has previously been held to be the case, erythrocytes used for hemolysis (penetration assay) contain the receptors in that small but definite amounts of Gal$\beta$Cer and Glc$\beta$Cer with 2-hydroxy acid have been found on human, bovine and porcine erythrocytes.

The general structural characteristics of the epithelial surface membrane of which the receptor glycolipids are an important part are relevant in the present context. A specific feature of the sphingolipid with its varying number of hydroxyl groups of the ceramide is the combined hydrogen bond donor and acceptor capacity (FIG. 8) making up one of three defined zones of the membrane (see reference 33). This is probably of decisive importance to membrane stability which depends on a laterally oriented network of hydrogen bonds. The data on the cell surface membrane available at present make it seem likely that the virus has developed a binding property which interferes with this stability through specific interaction with all three parts of an essential component of this network.

EXAMPLE 5

Study of the Binding of Sendai Virus to Non-Biological Synthetic Substances which are Analogues of the Natural Receptor A number of synthetic substances shown in Table 1 were analyzed for virus binding in the two assays described in Matarials and Methods. Table 5 summarizes the semiquantitative binding results from overlayering of Sendai virus to dilutions of the substance in question. The + signs do not correspond to those of Table 3 or 4 but are only for relative comparison within Table 5.

As shown, there is weak binding to No. 12, but not to Nos. 11, 13 or 14, indicating some preference for Glc$\beta$. The two-chain compounds are better binders (compare 15 with 13). However, most importantly, the sulphono analogues, Nos. 16–18, bind most strongly, the two-chain compounds being preferred. A more precise quantification by means of the quantitative binding assay described above shows that No. 18 has the same avidity as the corresponding natural receptor, No. 3 to Table 3, both represented by curve C in FIG. 4. These substances were designed on the basis of the research done on the natural receptors, and it is interesting to note that the properties and dimensions of the natural epitope (Example 3) and the specifications of receptor analogues are completely satisfied with these substances. Thus, the requirements to parts A, B and C (as explained above) and their relative dimensions are met although part B is non-chiral and carries one or two sulphono groups instead of a chiral part with an amide linkage and two hydroxyls. Evidently, the $\alpha$ side of the sugar is available for binding, which is the requirement outlined in Example 3. For these analogues, this is explained by the sulphono groups giving four only sites which by repulsion and possibly hydrogen bonding to water produce a much less dense packing of the molecules in the monolayer of the assays.

It further appears from Table 5 that several other synthetic substances do not bind the virus. This is due either to incomplete fulfilment of the requirements for B (substances Nos. 11, 13 and 14 which may be compared with substances Nos. 1, 3 and 4, respectively, of Table 3, which are good binders), or to close chain packing making the presentation of the $\alpha$side of A impossible in the absence of a conformation-determining factor like the 2-hydroxy fatty acid of the natural receptor.

TABLE 5

Synthetic receptor analogues used for inhibition or binding
(Sugars are of D configuration and in pyranose form)

| | | Inhibition |
|---|---|---|
| 1 | Gal or GalβCETE | − |
| 2 | Glc or GlcβCETE | − |
| 3 | Galβ1 → 4Glc or Galβ1 → 4GlcβCETE | − |
| 4 | GalβCETE—BSA | − |
| 5 | GlcβCETE—BSA | − |
| 6 | Galβ1 → 4GlcβOEt | − |
| 7 | Galβ1 → 4Glcβ → OCH$_2$CH(CH$_2$SO$_2$(CH$_2$)$_{10}$COOH)(CH$_2$SO$_2$(CH$_2$)$_7$CH$_3$) | − |
| 8 | Galβ1 → 4Glcβ → OCH$_2$CH(CH$_2$SO$_2$(CH$_2$)$_{10}$COOH)(CH$_2$SO$_2$(CH$_2$)$_{10}$COOH) | − |
| 9 | Galβ1 → 4Glcβ → OCH$_2$CH(CH$_2$SO$_2$(CH$_2$)$_{10}$CONH—BSA)(CH$_2$SO$_2$(CH$_2$)$_7$CH$_3$) | + |
| 10 | Galβ1 → 4GlcβCETE—BSA | − |

| | | Binding |
|---|---|---|
| 11 | GalβOTE | − |
| 12 | GlcβOTE | (+) |
| 13 | Galβ1 → 4GlcβOTE | − |
| 14 | Galα1 → 4GalβOTE | − |
| 15 | Galβ1 → 4Glcβ → OCH$_2$CH(CH$_2$S—(CH$_2$)$_{15}$CH$_3$)(CH$_2$S—(CH$_2$)$_{15}$CH$_3$) | + |
| 16 | Glcβ → OCH$_2$CH$_2$SO$_2$—(CH$_2$)$_{17}$CH$_3$ | + + |
| 17 | Glcβ → OCH$_2$CH(CH$_2$SO$_2$—(CH$_2$)$_{15}$CH$_3$)(CH$_2$SO$_2$—(CH$_2$)$_{15}$CH$_3$) | + + + |
| 18 | Galβ1 → 4Glc → OCH$_2$CH(CH$_2$SO$_2$—(CH$_2$)$_{15}$CH$_3$)(CH$_2$SO$_2$—(CH$_2$)$_{15}$CH$_3$) | + + + |

CETE: (OCH$_2$CH$_2$SCH$_2$CH$_2$CO$_2$CH$_3$)
OTE: (OCH$_2$CH$_2$S(CH$_2$)$_{17}$CH$_3$)
BSA: Bovine serum albumin.
−: no binding/inhibition; (+): weak binding; +: binding; + +: good binding; + + +: excellent binding.

EXAMPLE 6

Inhibition Experiments

Gal, Glc and Galβ1→4Glc in free form or derivatized or coupled to BSA (substances 1–6 and 10 to Table 5) were used in attempts to inhibit Sendai virus binding to receptors using mixtures of glycolipids as shown in FIG. 2, but also pure substances Nos. 1, 2 and 3 of Table 3 on thin-layer plates by preincubating the virus with the sugars before layering on the plate. There was no tendency of weakening of the autoradiographic spots, indicating that these substances were incapable of competing with the receptors for binding. The conclusion is that the carbohydrate part of the natural receptor substances in univalent or multivalent form is not in itself able to bind to the virus. Similarly, there was no inhibition in the microtiter assay using substance 3 of Table 3 as the receptor.

Preincubating Sendai virus wiht sonicated micelles of various membrane lipids gave a clear inhibition of virus binding on thin-layer plates for several glycolipids of Table 3. Also, in the plaque inhibition test, a rabies virus strain was shown to be completely inhibited by carefully sonicated liposomes containing substance 3 of Table 3. At similar dilution in the titration, liposomes containing phosphatidylserine gave no reduction of plaques.

Preincubation of Sendai virus with soluble receptor analogues (substances 7–9 of Table 5) before overlaying of virus on a thin-layer plate, or incubation in wells, gave the following results.

Sendai virus (60 μg) and substance 9 (1 mg) in 2 ml of PBS were preincubated for 1 hour at room temperature before overlayering on a thin-layer plate and incubation and working up as described in Materials and Methods, followed by autoradiography to detect bound virus. The glycolipid samples applied to the plate were total gangliosides of human erythrocytes (first-step receptor, see Example 1), and glycolipids 1, 2, 3 and 5 of Table 3, in addition to several suitable negative controls. Compared to the control plate (binding of virus without preincubation with substance 9 of Table 5), there was a significant reduction of virus binding after preincubation with substance 9, evaluated on the basis of the dark areas on the autoradiogram becoming lighter. Thus, binding to the glycolipids 1, 2 and 3 was reduced several times and the band for glycolipid 5 disappeared altogether. On the contrary, there was no effect on the binding to the first-step receptor (erythrocyte gangliosides, compare FIG. 1). Similar preincubations with 1 mg/ml of substances 7 and 8 gave no visible inhibition of virus binding. The conclusion from these experiments with the overlay assay is that the synthetic receptor analogue in multivalent form (substance 9 of Table 5), but not in univalent form (substances 7 and 8 of Table 5), is able to produce a selective inhibition of binding to the second-step receptor without having any effect on binding to the first-step receptor.

Preincubations of Sendai virus with these soluble receptor analogues using microtiter wells and an ELISA assay (see Materials and Methods) gave the following results. Preincubation with substance 9 of Table 5 gave a reduction of virus binding to the second-step receptor Galβ Cer ($A_{492}$=0.350 as a typical value at the highest concentration with a return to the maximum level after three 1:4 dilutions, see Materials and Methods). There was no inhibitory effect on the binding of virus to coated antiserum and there was no inhibition by preincubation with univalent analogue (substances 7 and 8). The results therefore coincide with those from the overlay assay above with a selective inhibition of binding to the second-step receptor, but not to the antibody, and a need for multivalency in order for the analogue to be effective.

BIBLIOGRAPHY

1. Lycke et al., eds., *Textbook of Medical Virology*, Butterworths, London, 1983.
2. Lycke et al., see 1. White et al., *Quart. Rev. Biophys.* 16, 1983, pp. 151–195.
3. Lonberg-Holm et al., eds., *Virus Receptors*, part 2, "Animal Viruses, Receptors and Recognition", ser. B, vol. 8, Chapman and Hall, London, 1981. Dimmock, *J. Gen. Virol.* 59, 1982, pp. 1–22.
4. Bell, *Biophys. J.* 45, 1984, pp. 1051–1064.
5. Lycke et al., see 1.
6. MacDonald et al., *Virology* 134, 1984, pp. 103–117.
7. Schlegel et al., *Cell* 32, 1983, pp. 639–646. Superti et al., *Arch. Virol.* 81, 1984, pp. 321–328.
8. Huang, J. Gen. *Virol.* 64, 1983, pp. 221–224. Huang, *Lipids* 18, 1983, pp. 489–492.
9. Paulsen, *Chem. Soc. Rev.* 13, 1984, pp. 15–45.
10. Lee et al., in Horowitz, ed., *The Glycoconjugates, Vol.* 4, Academic Press, New York, 1982, pp. 57–87. Dahmen et al., *Carbohydr. Res.* 127, 1984, pp. 27–33.
11. Lycke et al., see 1.
12. Middlebrook et al., *Microbiol. Rev.* 48, 1984, pp. 199–221.
13. Kanfer et al., eds., *Sphingolipid Biochemistry, Handbook of Lipid Research*, Vol. 3, Plenum Press, New York, 1983.
13a. Breimer et al., *J. Biol. Chem.* 257, 1982, pp. 557–568.
14. Breimer et al., in Quayle, ed., *Adv. Mass Spectrom.*, Heyden and Sons Ltd., London, Vol. 8B, 1980, pp. 1097–1108.
15. Falk et al., *Arch. Biochem. Biophys.* 192, 1979, pp. 164–202.
16. See Kanfer et al., 13.
17. Karlsson et al., *J. Lipid Res.* 12, 1971, pp. 466–472.
18. Karlsson et al., *Eur. J. Biochem.* 46, 1974, pp. 243–258.
19. Breimer et al., *Exp. Cell Res.* 135, 1981, pp. 1–13.
20. Breimer et al., *J. Biochem.* 90, 1981, pp. 589–609.
21. Karlsson et al., *Biochim. Biophys.* Acta 306, 1973, pp. 317–328.
22. see Huang, *Lipids*, ref. 8.
23. Hansson et al., in Chester et al., eds., *Glycoconjugates*, Proc. 7th Int. Sympos., Rahms, Lund, Sweden, 1983, pp. 631–632.
24. Magnusson et al., in Chester et al., eds., *Glycoconjugates*, Proc. 7th Int. Sympos., Rahms, Lund, Sweden, 1983, pp. 643–644.
25. Brown et al., in Chester et al., eds., *Glycoconjugates*, Proc. 7th Int. Sympos., Rahms, Lund, Sweden, 1983, pp. 678–679.
26. see ref. 3.
27. see 23 and 25.
28. see Dimmock, ref. 3.
29. see ref. 23.
30. see ref. 25.
31. Pascher et al., *Chem. Phys. Lipids* 20, 1977, pp. 175–191.
32. Skarjune et al., *Biochemistry* 21, 1982, pp. 3154–3160.
33. Karlsson, in Chapman, ed., *Biological Membranes*, Academic Press, London, Vol. 4, 1982, pp. 1–74.
34. see White et al. in ref. 2. see Dimmock in ref. 3.
35. Richardson et al., *Virology* 131, 1983, pp. 518–532.
36. see White et al., ref. 2.
37. see ref. 35.
38. Sebesan et al., *Can. J. Chem.* 62, 1984, pp. 1034–1045.
39. see ref. 31.
40. see ref. 33.
41. Hitchcock et al., eds., *Plant Lipid Biochemistry*, Academic Press, London, 1971.
42. Falk et al, *FEBS Lett.* 101, 1979, pp. 273–276.
43. Björk et al., in Cartron et al., eds., *Red Cell Membrane Glycoconjugates and Related Genetic Markers*, Libraire Arnette, Paris, 1983, pp. 125–137.

44. Hansson et al., *FEBS Lett.* 139, 1982, pp. 291-294.
45. Hansson et al., *Biochim. Biophys. Acta* 750, 1983, pp. 214-216.
46. Holgersson et al., in Koprowski et al. (eds.), Symposium on *World's Debt to Pasteur*, pp. 273-301, Alan R. Liss, New York, 1985, in press.

We claim:

1. A method of inhibiting the interaction between a cellular second-step viral binding receptor and a virus which comprises exposing the virus to a compound which preferentially binds the viral recognition site for the binding epitope of said cellular second step viral binding receptor, whereby the binding of the virus to the receptor is inhibited, said compound comprising a carbohydrate moiety, a hydrocarbon moiety of at least five carbon atoms, and an intermediate moiety comprising at least one sulfur-containing functional group selected from the group consisting of —S—, —SO— and —SO$_2$—.

2. The method of claim 1 wherein the intermediate moiety comprises at least one thioether function.

3. The method of claim 1 wherein the intermediate moiety comprises at least one sulfono function.

4. A method of inhibiting the interaction between a cellular second-step viral binding receptor and a virus which comprises exposing the virus to a compound which preferentially binds the viral recognition site for the binding epitope of said cellular second-step viral binding receptor, said compound comprising a carbohydrate moiety, a hydrophobic moiety, said hydrophobic moiety comprising a hydrocarbon moiety having at least one or more chains at least one chain having a length of at least five carbon atoms, and an intermediate polar moiety presenting at least two hydrogen bonding sites.

5. The method of claim 4 wherein said hydrogen bonding sites are provided by functional groups selected independently from the group consisting of amino, carbonyl, hydroxyl, sulfhydryl, sulfoxy or sulfonyl groups.

6. The method of claim 4 wherein the compound has a conformation substantially similar to that of the natural binding epitope carried by 1-O-beta-D-galactopyransoyl-N-(2-D-hydroxyalkanoyl)-1,3-D-dihydroxy-2-D-aminoalkane.

7. The method of claim 4 wherein the carbohydrate moiety comprises one or more saccharide units, and the saccharide unit nearest the intermediate polar moiety is a pentose, hexose or heptose in furanose or pyranose form.

8. The method of claim 7 wherein the carbohydrate moiety comprises a plurality of saccharide units including a first saccharide unit nearest the intermediate polar moiety and a second saccharide unit adjacent to the first saccharide unit, the second unit being connected by a 1→4 linkage to the first unit.

9. The method of claim 4 wherein the hydrocarbon moiety comprises at least 14 carbon atoms.

10. The method of claim 9 wherein the hydrocarbon moiety comprises 20-30 carbon atoms.

11. The method of claim 4 wherein the compound presents a binding epitope for the cellular second step viral binding receptor, said epitope having a length of about 15-20 Å and a width of about 8-10 Å.

12. The method of claim 4 wherein the hydrophobic moiety presents a hydrophobic surface with a surface area of at least 50 Å$^2$.

13. The method of claim 4 wherein the compound has a bent conformation.

14. The method of claim 8 wherein the carbohydrate moiety comprises no more than five saccharide units.

15. A method of inhibiting the interaction between a cellular second-step viral binding receptor and a virus which comprises exposing the virus to a composition comprising:
   (1) a compound consisting essentially of (A) a carbohydrate moiety, (B) an intermediate moiety comprising at least two hydrogen bonding sites, and (C) a hydrocarbon moiety comprising at least 14 carbon atoms, said intermediate moiety connecting said carbohydrate and hydrocarbon moieties, wherein the saccharide unit of said carbohydrate moiety which is nearest said intermediate moiety is a pentose, hexose or heptose in furanose or pyranose form, and if substituted the substituents do not block the alpha side of said nearest saccharide unit, said hydrogen bonding sites of said intermediate moiety being provided by one or more hydrogen bonding groups selected from the group consisting of amino, carbonyl, hydroxyl, sulfhydryl, sulfoxy or sulfone groups, said compound having a total length of about 15-20Å, said compound having a bent conformation; said compound specifically binding the viral recognition site for the binding epitope of said cellular second-step viral binding receptor and
   (2) a pharmaceutically acceptable vehicle or excipient.

* * * * *